US008936786B2

(12) United States Patent
Vol et al.

(10) Patent No.: US 8,936,786 B2
(45) Date of Patent: *Jan. 20, 2015

(54) METHODS AND COMPOSITIONS FOR ORAL ADMINISTRATION OF PROTEIN AND PEPTIDE THERAPEUTIC AGENTS

(75) Inventors: Alexander Vol, Rehovot (IL); Orna Gribova, Rehovot (IL)

(73) Assignee: Oshadi Drug Administration Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/811,871

(22) PCT Filed: Jan. 8, 2009

(86) PCT No.: PCT/IL2009/000036
§ 371 (c)(1),
(2), (4) Date: Aug. 3, 2010

(87) PCT Pub. No.: WO2009/087633
PCT Pub. Date: Jul. 16, 2009

(65) Prior Publication Data
US 2010/0297245 A1  Nov. 25, 2010

Related U.S. Application Data

(60) Provisional application No. 61/080,295, filed on Jul. 14, 2008.

(30) Foreign Application Priority Data

Jan. 8, 2008  (IL) .......................................... 188647

(51) Int. Cl.
| A61K 39/44 | (2006.01) |
| A61K 38/39 | (2006.01) |
| A61K 9/10 | (2006.01) |
| A61K 9/48 | (2006.01) |
| A61K 38/18 | (2006.01) |
| A61K 38/19 | (2006.01) |
| A61K 38/21 | (2006.01) |
| A61K 38/23 | (2006.01) |
| A61K 38/27 | (2006.01) |
| A61K 38/36 | (2006.01) |
| A61K 39/00 | (2006.01) |

(52) U.S. Cl.
CPC . *A61K 38/39* (2013.01); *A61K 9/10* (2013.01); *A61K 9/4891* (2013.01); *A61K 38/1816* (2013.01); *A61K 38/191* (2013.01); *A61K 38/21* (2013.01); *A61K 38/23* (2013.01); *A61K 38/27* (2013.01); *A61K 38/363* (2013.01)
USPC ..................... 424/178.1; 424/184.1

(58) Field of Classification Search
None
See application file for complete search history.

(56) References Cited

U.S. PATENT DOCUMENTS

| 3,252,859 | B1 | 4/1966 | Silver | |
| 5,145,684 | A * | 9/1992 | Liversidge et al. | ........... 424/489 |
| 5,462,866 | A | 10/1995 | Wang | |
| 5,843,509 | A | 12/1998 | Calvo Salve | |
| 5,874,105 | A | 2/1999 | Watkins | |
| 6,071,535 | A | 6/2000 | Hayward | |
| 6,171,586 | B1 * | 1/2001 | Lam et al. | .................. 424/130.1 |
| 6,228,377 | B1 | 5/2001 | Sebillotte-Arnaud | |
| 6,322,765 | B1 | 11/2001 | Muhlhofer | |
| 6,458,387 | B1 | 10/2002 | Scott | |
| 6,482,517 | B1 | 11/2002 | Anderson | |
| 6,528,497 | B1 | 3/2003 | Basten | |
| 6,548,264 | B1 * | 4/2003 | Tan et al. | ..................... 435/7.21 |
| 6,551,576 | B1 | 4/2003 | Unger | |
| 6,638,621 | B2 | 10/2003 | Anderson | |
| 6,656,922 | B2 | 12/2003 | Byun | |
| 6,667,060 | B1 | 12/2003 | Vandecruys | |
| 6,698,247 | B2 | 3/2004 | Tennent | |
| 6,808,720 | B2 | 10/2004 | Unger | |
| 6,989,195 | B2 | 1/2006 | Anderson | |
| 7,045,146 | B2 | 5/2006 | Caruso | |
| 7,083,572 | B2 | 8/2006 | Unger | |
| 7,090,868 | B2 | 8/2006 | Gower | |
| 7,105,229 | B2 | 9/2006 | Anderson | |
| 7,195,780 | B2 | 3/2007 | Dennis | |
| 7,316,818 | B2 | 1/2008 | Yatvin | |
| 7,351,741 | B2 | 4/2008 | Weidner | |
| 7,384,914 | B2 | 6/2008 | Goldberg | |
| 7,455,830 | B2 | 11/2008 | Sung | |

(Continued)

FOREIGN PATENT DOCUMENTS

| EP | 0491114 | 6/1992 |
| EP | 1179349 | 2/2002 |

(Continued)

OTHER PUBLICATIONS

Durand et al., Langmuir, 2004, vol. 20, p. 6956-6963.*
Chung et al., "Hydrophobic modification of silica nanoparticle by using aerosol spray reactor", Colloids and Surfaces A: Physicochem. Eng. Aspects 236:73-79 (2004).
Fu X. and Qutubuddin S., "Synthesis of titania-coated silica nanoparticles using a nonionic water-in-oil microemulsion", Colloids Surf. A: Physicochem. Eng. Aspects 179(1):65-70 (2001).

(Continued)

*Primary Examiner* — Yunsoo Kim
(74) *Attorney, Agent, or Firm* — Rodney J. Fuller; Booth Udall Fuller, PLC

(57) ABSTRACT

The present invention provides a pharmaceutical composition formulated for oral delivery, comprising a particulate non-covalently associated mixture of pharmacologically inert silica nanoparticles having a hydrophobic surface, a polysaccharide, and a biologically active protein or peptide suspended in an oil. The present invention further provides methods of manufacturing same and therapeutic methods utilizing same for oral delivery of a therapeutic protein or peptide.

11 Claims, 18 Drawing Sheets

(56) References Cited

U.S. PATENT DOCUMENTS

| | | |
|---|---|---|
| 7,470,663 B2 | 12/2008 | Ekwuribe |
| 2002/0150621 A1 | 10/2002 | Kohane |
| 2003/0035888 A1 | 2/2003 | Eriyama |
| 2003/0235619 A1 | 12/2003 | Allen |
| 2004/0091541 A1 | 5/2004 | Unger |
| 2004/0115264 A1 | 6/2004 | Blouquin |
| 2004/0242729 A1 | 12/2004 | Baran |
| 2005/0170004 A1 | 8/2005 | Rosenberger |
| 2006/0053971 A1 | 3/2006 | Sun |
| 2006/0083781 A1 | 4/2006 | Shastri |
| 2006/0177495 A1 | 8/2006 | Allen |
| 2006/0204559 A1 | 9/2006 | Bess |
| 2007/0098990 A1 | 5/2007 | Cook |
| 2007/0104778 A1 | 5/2007 | Zeng |
| 2007/0134332 A1 | 6/2007 | Turnell |
| 2007/0154559 A1* | 7/2007 | Pai et al. ............ 424/489 |
| 2007/0172426 A1 | 7/2007 | Lee |
| 2007/0184076 A1 | 8/2007 | Unger |
| 2007/0196656 A1 | 8/2007 | Rowell |
| 2007/0258889 A1 | 11/2007 | Douglas |
| 2007/0275969 A1 | 11/2007 | Gurny |
| 2010/0278922 A1 | 11/2010 | Vol |

FOREIGN PATENT DOCUMENTS

| | | |
|---|---|---|
| WO | 96/37232 | 11/1996 |
| WO | 03/066859 | 8/2003 |
| WO | 2005/094785 | 10/2005 |
| WO | 2006/062544 | 6/2006 |
| WO | 2006/097793 | 9/2006 |

OTHER PUBLICATIONS

Krysztafkiewicz A. et al., "Precipitated silicas modified with 3-aminopropyltriethoxysilane. Colloids Surf", A: Physicochem. Eng. Aspects 173:73-84 (2000).

Nadano D. et al., "Measurement of deoxyribonuclease I activity in human tissues and body fluids by a single radial enzyme-diffusion metho", Clinical Chemistry 39:448-52 (1993).

Okada M. et al., "Chemical Synthesis of Polysaccharides III. A Synthetic Polysaccharide Having One Hydroxyl Group in Its Repeating Unit, 3,4-Dideoxy-(1→6)-α-DL-threo-hexopyranan", Polymer journal 15(11):821-826 (1983).

Ou J. et al., "L-4F, an apolipoprotein A-1 mimetic, dramatically improves vasodilation in hypercholesterolemia and sickle cell disease", Circulation 107:2337-2341 (2003).

Zhang J. and Gao L., "Nanocomposite powders from coating with heterogeneous nucleation processing", Ceram. Int. 27(2):143-147 (2001).

Sihorkar and Vyas (2001) Potential of polysaccharide anchored liposomes in drug delivery, targeting and immunization. J Pharm Pharm Sci 4(2): 138-158.

Varshosaz (2007) Insulin Delivery Systems for Controlling Diabetes. Recent Patents on Endocrine, Metabolic & Immune Drug Discovery 1:25-40.

Bjork, Erik et al., "Starch Microspheres Induce Pulsatile Delivery of Drugs and Peptides Across the Epithelial Barrier by Reversible Separation of the Tight Junctions", J Drug Target, 2(6):501-507 (1995).

Eleftheriadou, I. et al., "The effects of medications used for the management of diabetes and obesity on postprandial lipid metabolism", Curr Diabetes Rev, 4(4):340-356 (2008).

Jean, J. and Yang, S., "Y2O2S:Eu Red Phosphor Powders Coated with Silica", J. Am. Ceram. Soc., 83(8):1928-1934 (2000).

Li, Chun-Lei and Deng, Ying-Jie, "Oil-based formulations for oral delivery of insulin", J Pharmand Pharmacol, 56(9):1101-1107 (2004).

Lin, Yu-Hsin et al., "Preparation and characterization of nanoparticles shelled with chitosan for oral insulin delivery", Biomacromolecules, 8(1):146-152 (2007).

Schipper, Nocolaas G. M. et al., "Chitosans as absorption enhancers for poorly absorbable drugs 2: mechanism of absorption enhancement", Pharm Res, 14(7):923-929 (1997).

Vaidya, H. B. et al., "Glucagon like peptides-1 modulators as newer target for diabetes", Curr Drug Targets, 9(10):911-920 (2008).

Ververidis, Filippos et al., "Biotechnology of flavonoids and other phenylpropanoid-derived natural products. Part I: Chemical diversity, impacts on plant biology and human health", Biothechnol J, 2(10):1214-1234 (2007).

Ververidis, Filippos et al., "Biotechnology of flavonoids and other phenylpropanoid-derived natural products. Part II: Reconstruction of multienzyme pathways in plants and microbes", Biothechnol J, 2(10):1235-1249 (2007).

Zhang, Ju-Xian and Gao, Long-Qiao, "Nanocomposite powders from coating with heterogeneous nucleation processing", Ceram Int, 27(2):143-147 (2001).

Lewis, Richard J. (ed) Hawley's Condensed Chemical Dictionary, 15th edition, 2007. Wiley-Interscience, entry for "amylopectin" p. 79 pp. 1-3.

ISR of PCT/IL2009/000036 mailed Apr. 24, 2009.

ISR of PCT/IL09/00037 mailed Jun. 25, 2009.

EP 09701269 Supplementary Search Report dated Aug. 2, 2011.

EP 09700655 Supplementary Search Report dated Dec. 16, 2011.

U.S. Appl. No. 12/811,859 Requirement for Restriction/Election dated Mar. 21, 2012.

U.S. Appl. No. 12/811,859 Non-Final Rejection dated Jul. 18, 2012.

Gurkov and Basheva (2006) Hydrodynamic behavior and stability of approaching deformable drops. In: Encyclopedia of Surface and Colloid Science; Somasundaran P (editor), vol. 4, 2nd edition, CRC Press, Taylor & Francis Group, FL, USA.

Lincopan et al., (2009) Silica-based cationic bilayers as immunoadjuvants. BMC Biotechnol 9: 5.

* cited by examiner

Ac-DKWKAVYDKFAEAFKEFL-NH₂    Ac-DWLKAFYDKVAEKFKEAF-NH₂

US 8,936,786 B2

METHODS AND COMPOSITIONS FOR ORAL ADMINISTRATION OF PROTEIN AND PEPTIDE THERAPEUTIC AGENTS

RELATED APPLICATION DATA

This application is the U.S. national stage of PCT/IL2009/000036, filed Jan. 8, 2009, which claims the benefit of U.S. Provisional Application No. 61/080,295, filed Jul. 14, 2008, and also claims priority to Israeli Application No. 188647 filed Jan. 8, 2008, the contents of each of which are herein incorporated by reference for all purposes.

FIELD OF INVENTION

The present invention relates to oral pharmaceutical compositions, comprising an intimate mixture of solid particulate ingredients within an oil carrier. Preferably the compositions are anhydrous. Specifically, the pharmaceutical compositions comprise a particulate non-covalently associated intimate mixture of pharmacologically inert silica nanoparticles having a hydrophobic surface, a polysaccharide, and a biologically active protein or peptide where the particulate mixture is suspended or embedded in an oil or mixture of oils. The present invention further provides methods of manufacturing same and therapeutic methods utilizing same for oral delivery of the active protein or peptide.

BACKGROUND OF THE INVENTION

Medical use of protein drugs is constrained by three major drawbacks. The first is their short biological half-life which requires, in some cases, frequent administrations. The second is the rapid degradation which occurs in mucosal tissues that generally cover the body cavities. Lastly, most protein drugs are large molecules and therefore do not easily cross the intestinal epithelium. As a result, the bioavailability of orally administered protein-based drugs is typically extremely low. Therefore, the most common mode of protein drugs administration is the parenteral route. However, apart from the inconvenience to the patients, parenteral delivery systems are also more expensive in terms of production and drug administration. There is therefore an unmet medical need for an effective non-parenteral mode of administration of protein drugs that will provide protection against biological degradation and/or enhance its transport across mucosal barriers. Although sophisticated non-parenteral pharmaceutical systems, such as intra-nasal systems, have been developed, oral administration is more favorable, having the major advantage of convenience for increased patient compliance.

DNase, for example, is unstable in the presence of water, oxidative stress, temperature fluctuations, and acid pH conditions. The maximal activity is observed within a pH range of 6-8. These characteristics create difficulties for oral DNase administration. The only currently available methods of delivering active DNase to the plasma are via injection (IV, SC or IM). RNase can be deactivated by mutual interaction between different regions of the RNase molecule, and thus requires formulations capable of preventing this type of interaction.

Examples of biologically active proteins include but are not limited to growth factors, cytokines, peptide hormones, analgesic peptides, enzymes, blood coagulating factors, peptide neurotransmitters, antibodies and may include synthetic polymers of amino acids. Specific examples of biologically active proteins or peptides include pituitary growth hormone, erythropoietin, DNase, RNase, and monoclonal antibodies among others.

Biopolymers and Their Use in Delivering Active Agents

Biopolymers such as polysaccharides have been known for many years. Polysaccharides are widely used as excipients in oral dosage forms, as disclosed for example in U.S. Pat. No. 6,667,060 to Vandecruys and US patent application 2004/0115264 to Blouquin. These references neither disclose nor suggest use of biopolymers in combination with nanoparticles or oil.

Nanoparticles and Their Use in Delivering Active Agents

Silica nanoparticles are well known in the art as pharmaceutical excipients and are their use is disclosed for example in U.S. Pat. No. 6,322,765 to Muhlhofer and U.S. Pat. No. 6,698,247 to Tennent, among many others. Coating of a nanoparticle-biopolymer complex with oil, or utility of same in oral administration of active agents are neither disclosed nor suggested.

Methods for imparting a hydrophobic surface to nanoparticles are well known in the art and are described, for example in Chung et al (Hydrophobic modification of silica nanoparticle by using aerosol spray reactor. Colloids and Surfaces A: Physicochem. Eng. Aspects 236 (2004) 73-79). Additional methods include the reverse micelles method (Fu X, Qutubuddin S, Colloids Surf. A: Physicochem. Eng. Aspects 179: 65, 2001), liquid precipitation method (Krysztafkiewicz A, Jesionowski T, Binkowski S, Colloids Surf. A: Physicochem. Eng. Aspects 173:73, 2000) and sol-gel method (Jean J, Yang S, J. Am. Ceram. Soc. 83(8):1928, 2000; Zhang J, Gao L, Ceram. Int. 27: 143, 2001). Use of the nanoparticles in combination with biopolymers, coating a nanoparticles-biopolymer complex with oil, or utility of same in oral administration of active agents are neither disclosed nor suggested.

U.S. Pat. Nos. 7,105,229, 6,989,195, 6,482,517, 6,638,621, 6,458,387, 7,045,146, and 5,462,866 among many others disclose use of nanoparticles or microparticles as excipients for proteins. These references neither disclose nor suggest intimate non-covalent association of nanoparticles with a biopolymer or embedding of a nanoparticle-polymer matrix in an oil coating.

US 2007/0154559 to Pai discloses an orally administrable composition containing nanoparticles comprising a charged water-soluble drug in complex with a counter-ion substance, a lipid, a polymer, and an emulsifier. The compositions are formed by (a) ionically bonding the drug with the counter-ion; (b) adding a lipid, a polymer, and a solubilizing agent; dissolving the whole mixture; and introducing the solution into an aqueous solution containing an emulsifier; and (c) removing the solubilizing agent. US 2006/0177495 and 2003/0235619 to Allen disclose delivery vehicles for delivering an active agent, comprising nanoparticles composed of a biodegradable hydrophobic polymer forming a core and an outer amphiphilic layer surrounding the polymer core and containing a stabilizing lipid.

US 2006/0083781 to Shastri discloses nanoparticles comprising a lipid and a polymer comprising an ionic or ionizable moiety. These compositions as well differ significantly from those of the present invention, inter alia in that (a) the polymer is not outside the nanoparticles but rather forms a part of them; and (b) the oil forms a part of the nanoparticles instead of coating the nanoparticle-polymer mixture. In addition, the unique structure of the matrix carrier compositions of the present invention is neither disclosed nor suggested.

WO 96/37232 to Alonso Fernandez discloses methods for preparation of colloidal systems through the formation of ionic lipid-polysaccharide complexes. The colloidal systems are stabilized through the formation of an ionic complex, at the interface, comprised of a positively charged aminopolysaccharide and a negatively charged phospholipid. These compositions as well differ significantly from those of the present invention, inter alia in that (a) the polymer is not outside the nanoparticles but rather forms a part of them; and (b) the oil forms a part of the nanoparticles instead of coating them. In addition, the unique structure of the matrix carrier of the present invention is neither disclosed nor suggested.

U.S. Pat. No. 6,548,264 to Tan et al. discloses silica-coated nanoparticles and a process for producing silica-coated nanoparticles. Silica-coated nanoparticles are prepared by precipitating nano-sized cores from reagents dissolved in the aqueous compartment of a water-in-oil microemulsion. A reactive silicate is added to coat the cores with silica. The silicate coating may further be derivatized with a protein. US 2007/0275969 to Gurny discloses pharmaceutical compositions for the oral administration of pharmaceutical agents having low water solubility. The pharmaceutical agents are solubilized with a polymer, from which nanoparticles are formed.

In cosmetics formulations, it is common to use compositions comprising water-in-oil emulsions containing an aqueous phase dispersed in an oily phase. There are numerous examples in which silica nanoparticles as well as polysaccharides are included in the liquid fatty phase. U.S. Pat. No. 6,228,377 for example, discloses water-in-oil emulsions containing a liquid fatty phase which contains hydrophobic or hydrophilic fumed silica, a branched polysaccharide alkyl ether, an emulsifying surfactant and oil. These compositions differ significantly from those of the present invention in that they include a water phase and surfactants that serve as the most important structure forming factor of the composition.

Additional Strategies

Methods for oral administration of biologically active proteins and peptides are the object of extensive research efforts but have been proven generally inefficient to date. A number of strategies for preventing degradation of orally administered proteins have been suggested, including use of core-shell particles (U.S. Pat. No. 7,090,868 to Gower) and nanotubes (U.S. Pat. No. 7,195,780 to Dennis). Liposomes have been used as a carrier for orally administered proteins, as well as aqueous emulsions and suspensions (U.S. Pat. No. 7,316,818; WO 06/062544; U.S. Pat. No. 6,071,535; and U.S. Pat. No. 5,874,105 to Watkins) and gas-filled liposomes (U.S. Pat. Nos. 6,551,576; 6,808,720; and 7,083,572 to Unger et al). Another composition comprises nanodroplets dispersed in an aqueous medium (US 2007/0184076). Additional strategies are found in WO 06/097793, WO 05/094785, and WO 03/066859 to Ben-Sason, which describe matrix-carriers containing peptide-effectors that provide penetration across biological barriers for administration of hydrophobic proteins; and EPO491114B1 to Guerrero Gomez-Pamo, which describes preparation of non-covalent protein-polysaccharide complexes for oral administration of biologically active substances, stabilized by precipitates of organic salts. None of these references discloses or suggests intimate non-covalent association of nanoparticles with a biopolymer or a nanoparticle-polymer matrix embedded in an oil coating.

In addition to the differences outlined above, none of the above references discloses or suggests the enhanced bioavailability of compositions of the present invention.

SUMMARY OF THE INVENTION

The present invention provides matrix carrier compositions, suitable for the oral delivery of a protein or peptide active agent comprising a particulate matter comprising pharmacologically inert nanoparticles having a hydrophobic surface, in intimate non-covalent association with a polysaccharide and the protein or peptide, wherein the particulate matter is suspended in, embedded in or dispersed in oil. The present invention further provides pharmaceutical compositions comprising a biologically active protein or peptide in association with this matrix carrier composition, methods of manufacturing same, pharmaceutical compositions comprising same in association with a biologically active protein, and therapeutic methods utilizing same.

An effective oral carrier for protein drugs should be able to shield its content against the luminal and brush border peptidases and be capable of facilitating the uptake of the protein drug, which is usually a large molecular weight entity, across the gastrointestinal (GI) epithelium. It is now disclosed for the first time that the compositions of the present invention surprisingly enable oral bioavailability of biologically active proteins and peptides. Whereas in prior art compositions very little if any therapeutic activity was achieved with oral formulations of peptide or protein agents, the present invention permits adsorption of the carried peptide or protein agent into the systemic circulation.

In one aspect, the present invention provides a matrix carrier composition for oral delivery of a protein or peptide active agent, comprising pharmacologically inert silica nanoparticles having a hydrophobic surface, wherein the size of the silica nanoparticles is between 1-100 nanometers, in intimate non-covalent association with at least one branched polysaccharide, and wherein the silica nanoparticle-polysaccharide complex is embedded in, dispersed in or suspended in oil. In another embodiment, the oil of the matrix carrier composition comprises a plurality of oils. In another embodiment, the weight of the particulate matter including the silica nanoparticles and the branched polysaccharide is not more than 25% of the overall weight of the composition. Preferably the weight of polysaccharides will be greater than the weight of the silica. In some embodiments the weight of the polysaccharides will be at least twice that of the silica, in other embodiments the weight of the polysaccharides will be 5 fold that of the silica in yet other embodiments the polysaccharides will be at least 10 times greater than the weight of silica nanoparticles. Each possibility represents a separate embodiment of the present invention.

In one preferred embodiment of the present invention, the polysaccharide comprises a branched polysaccharide. In another embodiment, the branched polysaccharide is selected from the group consisting of amylopectin, starch and glycogen. In another embodiment, the branched polysaccharide is starch.

In another aspect, the present invention provides a pharmaceutical composition comprising: (a) pharmacologically inert nanoparticles having a hydrophobic surface, wherein the size of the nanoparticles is between 1-100 nanometers, in intimate non-covalent association with a biopolymer comprising a polysaccharide; and (b) a biologically active protein or peptide non-covalently attached to the nanoparticles and the biopolymer; wherein the matrix formed by the nanoparticles, biopolymer, and biologically active protein or peptide is embedded in oil. According to currently preferred embodiments the biopolymer comprises a mixture of polysaccharides. According to currently more preferred embodiments the biopolymer includes at least one type of branched polysaccharide.

In one embodiment, the biologically active protein or peptide is non-covalently attached to the hydrophobic surfaces of the nanoparticles and the hydrophilic surfaces of the biopolymer. In another embodiment, the hydrophobic and hydrophilic portions of the biologically active protein or peptide make contact with the hydrophobic surfaces of the nanoparticles and hydrophilic surfaces of the biopolymer, respectively. In another embodiment, the hydrophobic portion of the biologically active protein or peptide is also non-covalently attached to hydrophobic portions of the biopolymer. Each possibility represents a separate embodiment of the present invention.

In another embodiment, the matrix carrier composition of the present invention is held together by non-covalent forces (FIG. 1). In another embodiment, the non-covalent forces between the components of the matrix composition enable the matrix composition to self-assemble when the components are blended together, as described herein. In another embodiment, the non-covalent forces cause the nanoparticles and biopolymer to form an intimate mixture. In another embodiment, the matrix composition exhibits an ordered, fractal structure. Each possibility represents a separate embodiment of the present invention.

In another embodiment, the nanoparticle-biopolymer complex is dispersed within the oil phase of the matrix composition. In another embodiment, the oil phase is impregnated with the nanoparticle-biopolymer complex of the matrix composition. As provided herein, the present invention provides compositions wherein the nanoparticles and biopolymer form a matrix that is impregnated and completely surrounded by the oil phase. Each possibility represents a separate embodiment of the present invention.

Reference to nanoparticles of the present invention as having a "hydrophobic" surface encompasses nanoparticles having a surface modified to be hydrophobic. In another embodiment, the nanoparticles are modified by coating the surface with a hydrocarbon. In another embodiment, the coating causes the nanoparticles to display hydrocarbon moieties on their surface. Methods for imparting a hydrophobic surface to nanoparticles are well known in the art, and are described inter alia herein. Each possibility represents a separate embodiment of the present invention.

In another embodiment, a pharmaceutical composition of the present invention comprises a mixture of oils selected from natural vegetable oils and synthetic analogues thereof.

In another embodiment, a matrix composition of the present invention further comprises an additional oil component. The term "additional oil component" encompasses an additional oil or mixture of oils, as described elsewhere herein. In another embodiment, the additional oil component comprises an antioxidant. Each possibility represents a separate embodiment of the present invention.

In another embodiment, a matrix composition of the present invention further comprises a third oil or mixture of oils in addition to the above-described additional oil or mixture of oils. In another embodiment, the third oil component comprises an antioxidant. Each possibility represents a separate embodiment of the present invention.

In another embodiment, a matrix composition of the present invention further comprises a wax.

In one embodiment, the protein or peptide of the pharmaceutical composition is erythropoietin. In another embodiment the protein or peptide is pituitary growth hormone. In another embodiment the protein or peptide is glatiramer acetate. In another embodiment, the protein or peptide is apolipoprotein A-1-mimetic peptide. In another embodiment, the protein or peptide is a monoclonal antibody. In another embodiment, the protein or peptide is a monoclonal antibody against the protein CD20. In another embodiment, the protein or peptide is selected from the group consisting of calcitonin, a tumor necrosis factor (TNF) protein, interferon-alpha, interferon-beta, and interferon-gamma. In another embodiment, a matrix composition of the present invention formulated for oral administration of the present invention is in a form selected from a soft gel capsule, a hard gelatin capsule, and a suspension.

In another embodiment, the present invention provides a method of administering a biologically active protein or peptide to a subject in need thereof, comprising orally administering to the subject a pharmaceutical composition of the present invention, thereby administering a biologically active protein or peptide to a subject.

In certain embodiments, the active protein or peptide ingredient in a pharmaceutical composition of the present invention is capable of reaching the bloodstream of a subject, following oral administration, with over 20% of the biological activity intact, preferably over 30% of the biological activity remains intact, more preferably at least 40% of the biological activity remains intact, most preferably at least 50% of the biological activity remains intact. In another embodiment, over 60% of the biological activity remains intact. In another embodiment, over 70% of the biological activity remains intact. In another embodiment, over 80% of the biological activity remains intact. In another embodiment, over 90% of the biological activity remains intact. Without wishing to be bound by any theory or mechanism of action, these properties are believed to be due to protection of the active agent from digestive enzymes and mechanical forces in the intestines by the excipients of pharmaceutical compositions of the present invention.

In some embodiments, a pharmaceutical composition of the present invention is designed to provide short-term release. "Short-term release", as used herein, refers to release within 8-12 hours, with maximal activity 4 hours after administration. In another embodiment, a pharmaceutical composition of the present invention is designed to provide medium-term release. "Medium-term release", as used herein, refers to release within 12-18 hours, with maximal activity 4-6 hours after administration. In another embodiment, a pharmaceutical composition of the present invention is designed to provide long-term release. "Long-term release", as used herein, refers to release within 18-48 hours, with maximal activity 4-8 hours after administration. In another embodiment, a pharmaceutical composition of the present invention is designed to provide very long-term release. "Very long-term release", as used herein, refers to release within 18-72 hours, with maximal activity 6-8 hours after administration. In another embodiment, the longer term-release compositions of the present invention exhibit a lower peak with a longer tail following the peak activity. Each possibility represents a separate embodiment of the present invention.

In another aspect, the present invention provides a method of manufacturing a matrix carrier composition, the method comprising the steps of: (a) dry mixing nanoparticles having a hydrophobic surface, wherein the size of the nanoparticles is between 1-100 nanometers, with a biopolymer comprising a polysaccharide, whereby the nanoparticles form an intimate non-covalent association with the biopolymer; and (b) mixing the nanoparticles and biopolymer into an oil. Preferably, the nanoparticles and biopolymer form a complex. In another embodiment, the complex is embedded in the oil. In another embodiment, the particle size of the matrix carrier composition is between 100-500,000 nanometers (nm). In some preferred embodiments, the particle size is between 100-50,000 nm. Each possibility represents a separate embodiment of the present invention.

In another embodiment, the present invention provides a method of manufacturing a pharmaceutical composition, the method comprising the steps of: (a) dry mixing pharmacologically inert nanoparticles having a hydrophobic surface, wherein the size of the nanoparticles is between 1-100 nanometers, with a biopolymer comprising a polysaccharide, whereby the nanoparticles form an intimate non-covalent association with the biopolymer; (b) dissolving or dispersing a biologically active protein or peptide into an oil; and (c) mixing the intimate mixture of nanoparticles and biopolymer into the oil, whereby the nanoparticles, biopolymer, and protein or peptide become embedded in the oil. Preferably, the nanoparticles, biopolymer, and protein or peptide form a complex. In another embodiment, the complex is embedded, dispersed, immersed or suspended in the oil. In another embodiment, the biologically active protein or peptide is attached to the hydrophobic surfaces of the nanoparticles and the hydrophilic surfaces of the biopolymer via non-covalent forces. In another embodiment, the particle size of the matrix carrier composition is between 100-50,000 nanometers. Each possibility represents a separate embodiment of the present invention.

It is to be explicitly understood that within the scope of the present invention, the compositions may comprise more than one biologically active protein or peptide. For example, each of the proteins or peptides may be mixed with at least one oil and then combined with the intimate mixture of dry particulate excipients. The oil or mixture of oils used for each protein or peptide may be the same or different. In alternative embodiments, two or more different peptides or proteins may be combined within a single mixture of solid particulate excipients and then mixed with the oil components. In alternative embodiments two or more active proteins or peptides may be individually combined with the particulate excipients and then these individual mixtures may be further mixed together with the oil components.

As provided herein, methods have been developed to formulate a variety of biologically active proteins and peptides in orally administrable form. In certain preferred embodiments, the components are blended in a particular order in order to produce oil-coated matrix carrier compositions that protect the active ingredient from digestive processes in the stomach and small intestine. The biopolymer, particularly when branched, absorbs hydraulic and mechanical stresses experienced during digestion. The oil coating constitutes a physical barrier that provides additional protection against digestive enzymes.

Further, without wishing to be bound by any theory or mechanism of action, matrix carrier compositions of the present invention are converted in the digestive system to particles smaller in size but similar in structure to the original composition (FIG. 2), which are absorbed similarly to chylomicrons and reach the bloodstream without undergoing first-pass metabolism in the liver. The biological activity of proteins and peptides is largely preserved following oral administration in the compositions of the invention.

DETAILED DESCRIPTION OF THE INVENTION

The present invention provides matrix carrier compositions, comprising pharmacologically inert nanoparticles having a hydrophobic surface, in intimate non-covalent association with a polysaccharide or high molecular weight structural protein, wherein the nanoparticle-containing complex is suspended in, embedded in, dispersed in oil. The present invention further provides pharmaceutical compositions comprising a biologically active protein or peptide in association with a matrix carrier composition, methods of manufacturing same, pharmaceutical compositions comprising same in association with a biologically active protein, and therapeutic methods utilizing same.

In one embodiment, the present invention provides a matrix carrier composition, comprising pharmacologically inert nanoparticles having a hydrophobic surface, in intimate non-covalent association with a biopolymer comprising a polysaccharide, wherein the diameter of the nanoparticles is between 1-100 nanometers, and the nanoparticle-biopolymer complex is embedded, dispersed, immersed or suspended in oil, and wherein the particle diameter of the matrix carrier composition is between 100-500,000 nanometers (nm). In certain preferred embodiments, the particle diameter is between 100-50,000 nm. In another embodiment, the oil phase of the matrix carrier composition comprises a plurality of oils. Each possibility represents a separate embodiment of the present invention.

Figure 1:
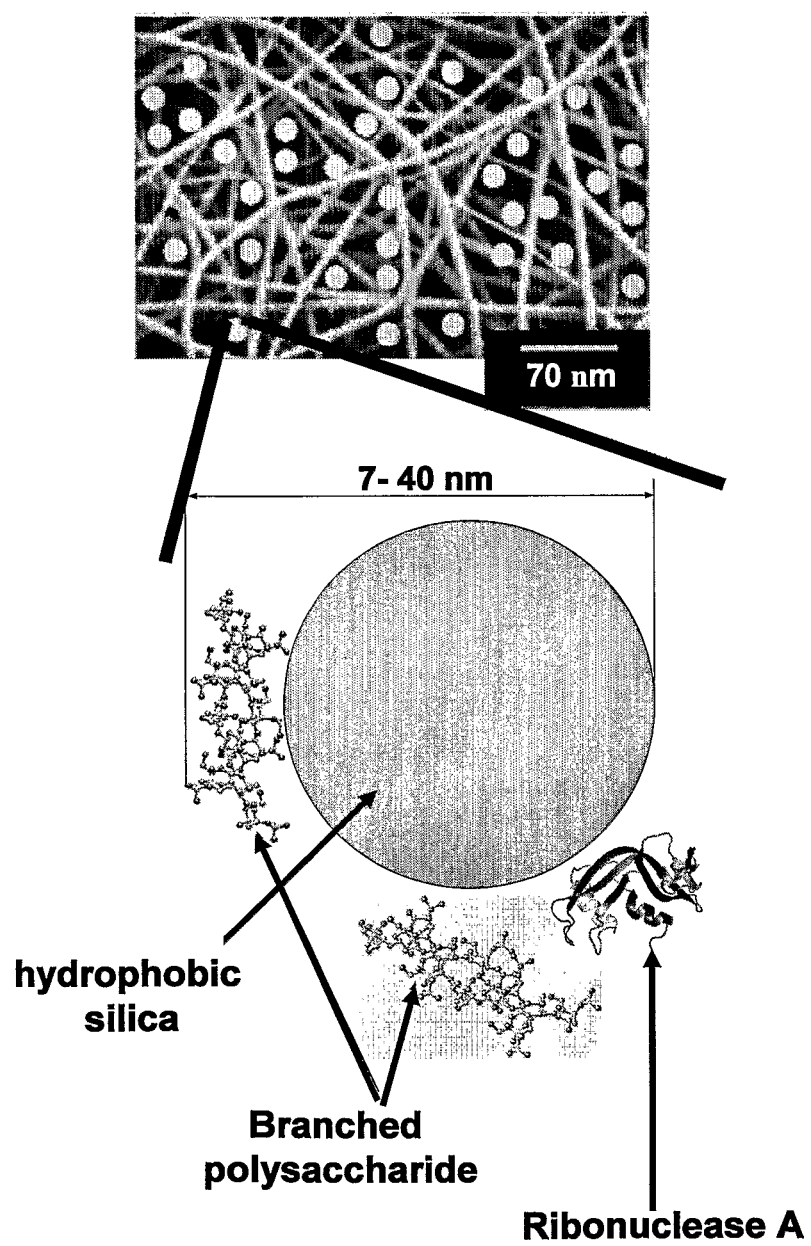
FIG. 1: Representative matrix-carrier structure containing ribonuclease and a polysaccharide. Top: Macrostructure containing branched fiber structure of the polysaccharide or biopolymer impregnated with hydrophobic silica nanoparticles. Bottom: Microstructure depiction.

In another embodiment, the matrix carrier composition is held together by non-covalent forces (FIG. 1). In another embodiment, without wishing to be bound by any theory or mechanism of action, the non-covalent forces between the components of the matrix composition enable the matrix composition to self-assemble when the components are mixed together, as described herein. In another embodiment, without wishing to be bound by any theory or mechanism of action, the matrix carrier includes a solid phase containing at least two solid pharmacologically inert materials (silica nanoparticles and polysaccharides) with different properties. In another embodiment, the non-covalent forces cause the nanoparticles and biopolymer to form an intimate mixture. In another embodiment, the matrix composition exhibits an ordered, fractal structure. Each possibility represents a separate embodiment of the present invention.

In another embodiment, the nanoparticle-biopolymer complex is dispersed within the oil phase of the matrix composition. In another embodiment, the oil phase is impregnated with the nanoparticle-biopolymer complex of the matrix composition. As provided herein, the present invention provides compositions wherein the nanoparticles and biopolymer form a matrix that is impregnated and completely surrounded by the oil phase. Each possibility represents a separate embodiment of the present invention.

Oil having particulate matter embedded, dispersed, immersed or suspended therein, as used herein, refers to particulate matter that is in contact with oil. The composition as a whole need not be homogeneous with regard to the distribution of the particulate matter. Rather, the particulate matter is capable of being embedded, dispersed, immersed or suspended in the oil when agitated. The particulate matter need not be completely homogeneous, but rather is characterized by its containing the ingredients specified herein and its intimate contact with the oil of the present invention. Compositions wherein the particulate matter is agglomerated fall within the scope of the present invention.

Nanoparticles

The nanoparticles of methods and compositions of the present invention are preferably pharmacologically inert. In another embodiment, the nanoparticles are composed of materials that are generally recognized as safe (GRAS). In another embodiment, the nanoparticles are non-toxic. In another embodiment, the nanoparticles are non-teratogenic. In another embodiment, the nanoparticles are biologically inert. Each possibility represents a separate embodiment of the present invention.

In another embodiment, the nanoparticles are silica nanoparticles. In one preferred embodiment, the nanoparticles are fumed silica nanoparticles. In another embodiment, the nanoparticles are composed of zinc oxide. In another embodiment, the nanoparticles are composed of carbon. In another embodiment, the nanoparticles are composed of titanium. In another embodiment, the nanoparticles are composed of another substance with hardness similar to that of silica nanoparticles. Each possibility represents a separate embodiment of the present invention.

In another embodiment, the nanoparticles are silica-containing nanoparticles. "Silica-containing nanoparticles" refers preferably to nanoparticles comprising silica, a silicate, or a combination thereof. "Silica" refers to silicon dioxide. Silica-containing nanoparticles are available commercially, e.g. as 99.99% pure finely ground silica. It will be understood by those skilled in the art that lower grades of purity of silica are also compatible with the present invention. "Silicate" refers to a compound containing silicon and oxygen, e.g. in tetrahedral units of $SiO_4$. In another embodiment, the term refers to a compound containing an anion in which one or more central silicon atoms are surrounded by electronegative ligands. Non-limiting examples of silicates are hexafluorosilicate, sodium silicate ($Na_2SiO_3$), aluminum silicates, magnesium silicates, etc. It is to be understood that the nanoparticles in structures of the present invention can be either of a single type or of multiple types, provided that, if multiple types are present, at least one type is a silica-containing nanoparticles. In another embodiment, essentially all the nanoparticles are silica-containing nanoparticles. Silica is widely recognized as a safe food additive (Thirteenth report of the Joint FAO/WHO Expert Committee on Food Additives, FAO Nutrition Meetings Report Series; from the Joint FAO/WHO Expert Committee on Food Additives meeting in Rome, May 27-Jun. 4, 1969). Each possibility represents a separate embodiment of the present invention.

Reference to nanoparticles of the present invention as having a "hydrophobic" surface indicates, in one embodiment, that at least 40% of the nanoparticle surface is hydrophobic. In another embodiment, at least 50% of the surface is hydrophobic. In another embodiment, at least 60% of the surface is hydrophobic. In another embodiment, at least 70% of the surface is hydrophobic. In another embodiment, at least 80% of the surface is hydrophobic. In another embodiment, at least 90% of the surface is hydrophobic. In another embodiment, at least 95% of the surface is hydrophobic. In another embodiment, 40-100% of the surface is hydrophobic. In another embodiment, 50-100% of the surface is hydrophobic. In another embodiment, 60-100% of the surface is hydrophobic. In another embodiment, 70-100% of the surface is hydrophobic. In another embodiment, 80-100% of the surface is hydrophobic. In another embodiment, 90-100% of the surface is hydrophobic. In another embodiment, 95-100% of the surface is hydrophobic. In another embodiment, 40-60% of the surface is hydrophobic. In another embodiment, 40-50% of the surface is hydrophobic. In another embodiment, 40-70% of the surface is hydrophobic. In another embodiment, 40-80% of the surface is hydrophobic. Each possibility represents a separate embodiment of the present invention.

In another embodiment, reference to nanoparticles as having a "hydrophobic" surface encompasses nanoparticles having a surface modified to be hydrophobic. In another embodiment, the nanoparticles are modified by coating the surface with a hydrocarbon. In another embodiment, the coating causes the nanoparticles to display hydrocarbon moieties on their surface. In another embodiment, the hydrocarbon moieties are selected from the group consisting of methyl, ethyl, propyl, isopropyl, butyl, isobutyl, T-butyl, pentyl, and isopentyl. In another embodiment, the coating causes the nanoparticles to display methyl moieties on their surface. Methods for imparting a hydrophobic surface to nanoparticles are well known in the art, and are described inter alia herein. As is known in the art it is possible to chemically modify the surface of the fumed silica by chemical reaction, generating a decrease in the number of silanol groups. In particular, silanol groups can be substituted with hydrophobic groups to obtain a hydrophobic silica. The hydrophobic groups can be: trimethylsiloxy groups, which are obtained in particular by treatment of fumed silica in the presence of hexamethyldisilazane. Silicas thus treated are known as "silica silylate" according to the CTFA (6th edition, 1995). They are sold, for example, under the references "Aerosil R812®" by the company Degussa and "CAB-OSIL TS-530®" by the company Cabot; dimethylsilyloxy or polydimethylsiloxane groups, which are obtained in particular by treatment of fumed silica in the presence of polydimethylsiloxane or dimethyldichlorosilane. Silicas thus treated are known as "silica dimethyl silylate" according to the CTFA (6th edition, 1995). They are sold, for example, under the references "Aerosil R972®.", "Aerosil R974®" by the company Degussa, "CAB-O-SIL TS-610®." and "CAB-O-SIL TS-720®.", by the company Cabot. Each possibility represents a separate embodiment of the present invention.

In another embodiment, nanoparticles of compositions of the present invention are practically insoluble in water. "Practically insoluble" refers, in another embodiment, to a substance having a solubility of less than 100 parts per million weight/weight (ppm). In another embodiment, the term refers to a solubility of less than 200 ppm. In another embodiment, the term refers to a solubility of less than 80 ppm. In another embodiment, the term refers to a solubility of less than 60 ppm. In another embodiment, the term refers to a solubility of less than 50 ppm. In another embodiment, the term refers to a solubility of less than 40 ppm. In another embodiment, the term refers to a solubility of less than 30 ppm. In another embodiment, the term refers to a solubility of less than 20 ppm. In another embodiment, the term refers to a solubility of less than 15 ppm. In another embodiment, the term refers to a solubility of less than 10 ppm. Each possibility represents a separate embodiment of the present invention.

In another embodiment, the diameter of nanoparticles of methods and compositions of the present invention is between 5-30 nanometers inclusive. In another embodiment, the diameter is between 7-40 nanometers (nm) inclusive. In another embodiment, the diameter is between 2-400 nm inclusive. In another embodiment, the diameter is between 2-300 nm inclusive. In another embodiment, the diameter is between 3-200 nm inclusive. In another embodiment, the diameter is between 4-150 nm inclusive. In another embodiment, the diameter is between 4-100 nm inclusive. In another embodiment, the diameter is between 5-50 nm inclusive. In another embodiment, the diameter is between 5-40 nm inclusive. In another embodiment, the diameter is between 6-25 nm inclusive. In another embodiment, the mean diameter of hydrophobic silica nanoparticles used in the present invention is 10-11 nm. In another embodiment, the average diameter is about 5 nm. In another embodiment, the average diameter is about 6 nm. In another embodiment, the average diameter is about 7 nm. In another embodiment, the average diameter is about 8 nm. In another embodiment, the average diameter is about 9 nm. In another embodiment, the average diameter is about 10 nm. In another embodiment, the average diameter is about 12 nm. In another embodiment, the average diameter is about 14 nm. In another embodiment, the average diameter is about 16 nm. In another embodiment, the average diameter is about 18 nm. In another embodiment, the average diameter is about 20 nm. In another embodiment, the average diameter is another diameter falling within a range disclosed herein. Each possibility represents a separate embodiment of the present invention.

In another embodiment, nanoparticles of the present invention fall within a range of melting temperatures particularly suitable for compositions of the present invention. In specific embodiments, the nanoparticles have a melting temperature ($T_m$) of over 600° C. In another embodiment, the $T_m$ is between 600-4500° C. Preferably, the $T_m$ is between 800-4500° C. In another embodiment, the $T_m$ is any $T_m$ falling within a range disclosed herein. Each possibility represents a separate embodiment of the present invention.

Imparting a Hydrophobic Surface to a Nanoparticle

Methods for imparting a hydrophobic surface to nanoparticles are well known in the art and are described inter alia, in Chung et al (Hydrophobic modification of silica nanoparticle by using aerosol spray reactor. Colloids and Surfaces A: Physicochem. Eng. Aspects 236 (2004) 73-79). Additional methods include the reverse micelles method (Fu X, Qutubuddin S, Colloids Surf. A: Physicochem. Eng. Aspects 179: 65, 2001), liquid precipitation method (Krysztafkiewicz A, Jesionowski T, Binkowski S, Colloids Surf. A: Physicochem. Eng. Aspects 173:73, 2000) and sol-gel method (Jean J, Yang S, J. Am. Ceram. Soc. 83(8):1928, 2000; Zhang J, Gao L, Ceram. Int. 27: 143, 2001).

Additional methods are described in US 2007/0172426 provides methods of imparting a hydrophobic surface to a nanoparticle, by combining them with a material having a first end that adsorbs to the surface of the nanoparticle and a second end that extends away from the nanoparticle and imparts hydrophobicity to the particles. The material may be a generally aliphatic compound having a polar end-group. The first end of each molecule of the compound may include a carboxyl group, an amine group, a silane, etc., that adsorbs to the surface of the particle. The second end of each molecule of the compound may include alkane group that extends away from the particle. Materials used to provide the hydrophobic surface layer include saturated fatty acids such as lauric acid, myristic acid, palmitic acid, and stearic acid, and unsaturated variants thereof, such as palmitoleic acid, oleic acid, linoleic acid, and linolenic acid. Silanes such as octadecyl trichlorosilane can also be widely used to functionalize oxide surfaces. The hydrophobic surface layer is provided by mixing the nanoparticles into a volume of hydrophobic coating material suitable for coating the particles. An excess of hydrophobic coating material is generally used so that the nanoparticles form a suspension in the hydrophobic coating material. Each nanoparticle then exhibits a hydrophobic layer on its surface. Additional methods for utilizing a hydrocarbon surfactant to coat nanoparticles are described in US 2006/0053971. Additional methods are described in US 2007/0098990. The disclosed methods utilize multiple organic acids in which the first acid is a low molecular weight organic carboxylic acid and the second acid is a high molecular weight organic carboxylic acid. The contents of each of the above patent applications are hereby incorporated by reference.

Biopolymers

A biopolymer of methods and compositions of the present invention is preferably a branched biopolymer. "Branched" as used herein encompasses both polymers that are naturally branched and those engineered to be branched by physical treatment such as thermal and/or ultrasound treatment. In general, branched polymers are defined as polymers wherein a substituent of a monomer subunit is replaced by another covalently bonded chain of the polymer. In another embodiment, the branched biopolymer is a crosslinked polymer. In another embodiment, the branched biopolymer is not crosslinked. Non-limiting examples of branched polymers are glycogen and amylopectin, forms of starch found in animals and plants, respectively. Structures of glycogen and amylopectin are depicted below:

ing temperature under 400° C. In another embodiment, the $T_m$ is below 350° C. In another embodiment, the $T_m$ is below 300° C. In another embodiment, the $T_m$ is below 250° C. In another embodiment, the $T_m$ is below 200° C. In another embodiment, the $T_m$ is below 150° C. In another embodiment, the $T_m$ is between 100-400° C. In another embodiment, the $T_m$ is any $T_m$ falling within a range disclosed herein. Each possibility represents a separate embodiment of the present invention.

Preferably, the biopolymer of methods and compositions of the present invention is selected from the group consisting of a polysaccharide and a high MW structural protein.

Polysaccharides

"Saccharide" refers to any simple carbohydrate including monosaccharides, monosaccharide derivatives, monosaccharide analogs, sugars, including those, which form the individual units in a polysaccharide. "Monosaccharide" refers to polyhydroxyaldehyde (aldose) or polyhdroxyketone (ketose) and derivatives and analogs thereof.

"Polysaccharide" refers to polymers formed from about 500 to over 100,000 saccharide units linked to each other by hemiacetal or glycosidic bonds. The polysaccharide may be

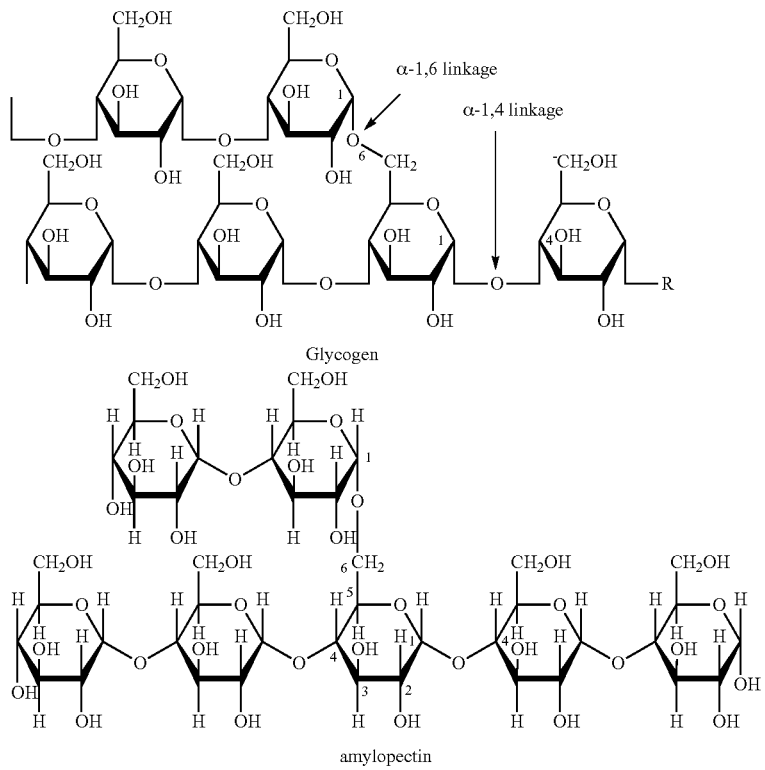

In another embodiment, the biopolymer is a fibrous biopolymer. "Fibrous polymer" refers to a polymer in the form of a network of discrete thread-shaped pieces. Non-limiting examples of fibrous polymers are guar gum (found e.g. in Benefiber™), collagen, keratin, fibrin, and elastin. Biopolymers can be either naturally fibrous or made fibrous by physical and chemical treatment.

Each type of branched and fibrous biopolymer represents a separate embodiment of the present invention.

In another embodiment, the biopolymer of a composition of the present invention falls within a range of melting temperatures particularly suitable for compositions of the present invention. In another embodiment, the biopolymer has a melteither a straight chain, singly branched, or multiply branched wherein each branch may have additional secondary branches, and the monosaccharides may be standard D- or L-cyclic sugars in the pyranose (6-membered ring) or furanose (5-membered ring) forms such as D-fructose and D-galactose, respectively, or they may be cyclic sugar derivatives, for example amino sugars such as D-glucosamine, deoxy sugars such as D-fucose or L-rhamnose, sugar phosphates such as D-ribose-5-phosphate, sugar acids such as D-galacturonic acid, or multi-derivatized sugars such as N-acetyl-D-glucosamine, N-acetylneuraminic acid (sialic acid), or N-sulfato-D-glucosamine. When isolated from nature, polysaccharide preparations comprise molecules that are heterogeneous in molecular weight. Polysaccharides include, among other compounds, galactomanans and galactomannan derivatives; galacto-rhamnogalacturons and galacto-rhamnogalacturon derivatives, and galacto-arabinogalacturon and galacto-arabinogalacturon derivatives.

The polysaccharide used in methods of the present invention is, in another embodiment, a naturally-occurring polysaccharide. In another embodiment, the polysaccharide is a synthetic polysaccharide. Non limiting examples of synthetic polysaccharides can be found in U.S. Pat. No. 6,528, 497 and in Okada M. et al. Polymer journal, 15 (11); 821-26 (1983). In another embodiment, the polysaccharide is a branched polysaccharide. This term is well understood to those skilled in the art and can refer to any number and structure of branches in the links between monosaccharide monomers. In another embodiment, the polysaccharide is a naturally-occurring branched polysaccharide. In another embodiment, the polysaccharide is a synthetic branched polysaccharide. Each possibility represents a separate embodiment of the present invention.

In another embodiment, the average MW of the polysaccharide is at least 100 kilodalton (kDa). In another embodiment, the average MW is at least 150 kDa. In another embodiment, the average MW is at least 200 kDa. In another embodiment, the average MW is at least 300 kDa. In another embodiment, the average MW is at least 400 kDa. In another embodiment, the average MW is at least 500 kDa. In another embodiment, the average MW is at least 600 kDa. In another embodiment, the average MW is at least 800 kDa. In another embodiment, the average MW is at least 1000 kDa. In another embodiment, the average MW is between 100-1000 kDa. In another embodiment, the average MW is between 150-1000 kDa. In another embodiment, the average MW is between 200-1000 kDa. In another embodiment, the average MW is between 100-800 kDa. In another embodiment, the average MW is between 100-600 kDa. Each possibility represents a separate embodiment of the present invention.

In another embodiment, the polysaccharide is selected from the group consisting of starch, dextrin, cellulose, chitin, alpha glucan, and beta glucan and derivatives thereof. Typically, cellulose, dextrin, starch and glycogen are all polymers of glucose and thus have the formula $(C_6H^{10}O_5)_n$.

In another embodiment, the polysaccharide is a starch, which has the structure below. Non-limiting examples of starch are corn starch, potato starch, rice starch, wheat starch, purum starch, and starch from algae. In another embodiment, the starch is any other starch known in the art. Each possibility represents a separate embodiment of the present invention.

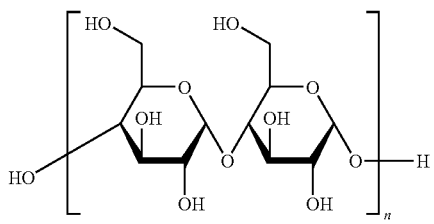

In another embodiment, the polysaccharide is a dextrin. "Dextrin" in another embodiment refers to a low-molecular-weight carbohydrate produced by the hydrolysis of starch. In another embodiment, the term refers to a linear α-(1,4)-linked D-glucose polymer starting with an α-(1,6) bond or a mixture of same. Dextrins are widely commercially available and can be produced inter alia by digestion of branched amylopectin or glycogen with α-amylase. A non-limiting example of a dextrin is a maltodextrin having the structure below. In another embodiment, the dextrin is any other dextrin known in the art. Each possibility represents a separate embodiment of the present invention.

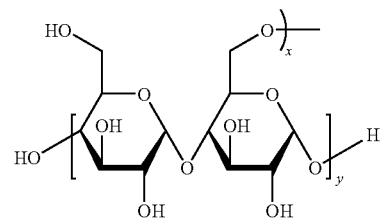

In another embodiment, the polysaccharide is cellulose. A non-limiting example of a starch is α-cellulose, which has the structure below. In another embodiment, the cellulose is any other cellulose known in the art. Each possibility represents a separate embodiment of the present invention.

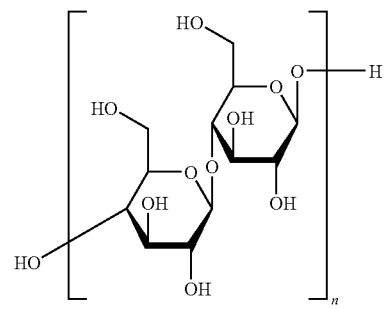

In another embodiment, the polysaccharide is chitin. A non-limiting example of chitin has the molecular formula $(C_8H_{13}NO_5)_n$ and has the structure below. In another embodiment, the chitin is any other chitin known in the art. Each possibility represents a separate embodiment of the present invention.

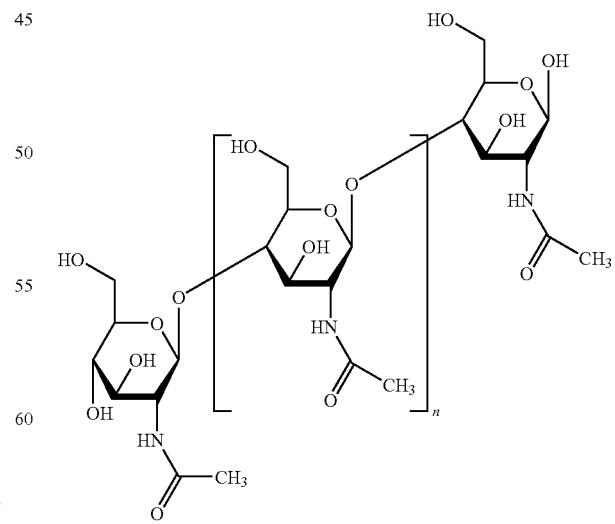

In another embodiment, the polysaccharide is an alpha-glucan. Alpha-glucans of the present invention may be linear or branched polymers of glucose with alpha 1-2, alpha 1-3, alpha 1-4, and/or alpha 1-6 glycosidic linkages. For example, alpha-glucans such as alpha-amylose derived from plants are unbranched linear glucose polymers with alpha 1-4 glycosidic linkages and alpha-glucans such as amylopectin are derived from plants are branched glucose polymers with alpha 1-4 glycosidic linkages in the backbone and alpha 1-6 linkages at branch points. In another embodiment, the alpha-glucan is any other alpha-glucan known in the art. Each possibility represents a separate embodiment of the present invention.

In another embodiment, the polysaccharide is a beta-glucan. "Beta-glucan" refers to those polysaccharides which comprise D-glucopyranosyl units which are linked together by (1→3) or (1→4) beta-linkages. Beta-Glucans occur naturally in many cereal grains such as oats and barley. The molecular weight of beta-glucan molecules occurring in cereals is typically 200 to 2000 kDa. In another embodiment, the beta-glucan is any other beta-glucan known in the art. Each possibility represents a separate embodiment of the present invention.

In another embodiment, the $T_m$ of a polysaccharide of a composition of the present invention falls within a range of melting temperatures particularly suitable for compositions of the present invention. In another embodiment, the polysaccharide has a $T_m$ under 400° C. In another embodiment, the $T_m$ is another $T_m$ or range of $T_m$ defined herein. Each possibility represents a separate embodiment of the present invention.

In another embodiment, a pharmaceutical composition of the present invention further comprises an additional biopolymer that is a linear biopolymer. In another embodiment, the additional biopolymer is a linear polysaccharide. In another embodiment, the additional biopolymer is a linear high molecular weight structural protein. In another embodiment, the additional biopolymer is selected from the group consisting of chitin, cellulose, a linear alpha glucan, and a linear beta glucan. In another embodiment, the additional biopolymer is selected from the group consisting of chitin, amylose, cellulose, and beta glucan. A non-limiting example of such a combination is amylopectin, a branched biopolymer, and chitin, a linear polysaccharide. Other branched and linear biopolymers disclosed herein are suitable as well. Each possibility represents a separate embodiment of the present invention.

In another embodiment of methods and compositions of the present invention, the biopolymer of the composition is a linear polysaccharide. In this embodiment, a branched biopolymer is not required to be present.

In another embodiment, the additional biopolymer of methods and compositions of the present invention is a fiber, preferentially a dietary fiber. The definition of the term "fiber" and "dietary fiber" as used herein includes unavailable carbohydrates, indigestible residue, and plant cell polysaccharides and lignin, all of which are resistant to hydrolysis by human digestive enzymes. Preferred fibers are members selected from the group consisting of guar gum, pectin, fructo-oligosaccharides and derivatives thereof. Small amounts of other indigestible compounds, such as phytates, tannins, saponins and cutin, may be included in dietary fiber since these compounds are indigestible and associated with dietary fiber polysaccharides. In another embodiment, the dietary fiber is an insoluble fiber. In another embodiment, the dietary fiber is a linear insoluble fiber. In another embodiment, the dietary fiber is a soluble fiber. In another embodiment, the dietary fiber is a linear soluble fiber. Each possibility represents a separate embodiment of the present invention.

In another embodiment, a composition of the present invention comprises a branched biopolymer, a linear polysaccharide, and an insoluble fiber. In another embodiment, a composition of the present invention comprises a branched biopolymer, a polypeptide, and an insoluble fiber. An example of such is a composition comprising amylopectin, a branched polysaccharide; keratin, a polypeptide; and cellulose, an insoluble fiber. Other branched polysaccharides, polypeptides, and insoluble fibers disclosed herein are suitable as well. In another embodiment, a composition of the present invention comprises a branched polysaccharide, a linear polysaccharide, and an insoluble fiber. An example of such is a composition comprising amylopectin, a branched polysaccharide; chitin, a linear polysaccharide; and cellulose, an insoluble fiber. Other branched and linear polysaccharides and insoluble fibers disclosed herein are suitable as well. Each possibility represents a separate embodiment of the present invention.

Structural Proteins

According to certain embodiments the dry solid particulate ingredients of compositions may further comprise a structural protein. The structural protein of methods and compositions of the present invention is a high molecular weight (MW) structural protein. In some embodiments, the structural protein comprises both hydrophilic and hydrophobic residues that interact with the hydrophobic and hydrophilic regions, respectively, of the biologically active protein or peptide.

In another embodiment, the average MW of the structural protein is at least 100 kilodalton (kDa). In another embodiment, the average MW is at least 150 kDa. In another embodiment, the average MW is at least 200 kDa. In another embodiment, the average MW is at least 300 kDa. In another embodiment, the average MW is at least 400 kDa. In another embodiment, the average MW is at least 500 kDa. In another embodiment, the average MW is at least 600 kDa. In another embodiment, the average MW is at least 800 kDa. In another embodiment, the average MW is at least 1000 kDa. In another embodiment, the average MW is between 100-1000 kDa. In another embodiment, the average MW is between 150-1000 kDa. In another embodiment, the average MW is between 200-1000 kDa. In another embodiment, the average MW is between 100-800 kDa. In another embodiment, the average MW is between 100-600 kDa. Each possibility represents a separate embodiment of the present invention.

"Structural protein", in one embodiment, refers to a protein included for the structure it confers to the matrix carrier composition. In another embodiment, a structural protein of the present invention lacks therapeutic activity. In another embodiment, the term refers to a protein that confers structure to a cell, cellular membrane, or extracellular membrane in vivo. In another embodiment, the structural protein is a fibrous protein. In another embodiment, the structural protein is a scleroprotein. In another embodiment, the structural protein is selected from the group consisting of elastin, collagen, keratin, and fibrinogen. In another embodiment, the structural protein is any other fibrous protein or scleroprotein known in the art. Each possibility represents a separate embodiment of the present invention.

In another embodiment, the structural protein is elastin. Non-limiting examples of elastin proteins are described, inter alia, in GenBank Accession numbers NP_031951, NP_786966, and AAC98394. In another embodiment, the elastin is any other elastin known in the art. Each possibility represents a separate embodiment of the present invention.

In another embodiment, the structural protein is collagen. Non-limiting examples of collagen proteins include those encoded by gene symbols COL3A1, COL14A1, COL11A2, COL5A2, COL11A1, COL5A1, COL4A6, COL4A5, COL4A4, COL4A3, COL4A2, COL1A2, COL5A3, COL18A1, COL12A1, COL19A1, COL24A1, COL4A1, and COL2A 1. In another embodiment, the collagen is any other collagen known in the art. Each possibility represents a separate embodiment of the present invention.

In another embodiment, the structural protein is keratin. Non-limiting examples of keratin proteins include keratin 18, keratin 14, keratin 3, and keratin 86 (GenBank Accession numbers P05783, P02533, P12035, O43790, respectively. In another embodiment, the keratin is any other keratin known in the art. Each possibility represents a separate embodiment of the present invention.

In another embodiment, the structural protein is fibrinogen. Fibrinogen is a glycoprotein composed of three pairs of polypeptides: two alpha, two beta, and two gamma chains. Non-limiting examples of the fibrinogen alpha, beta, and gamma chains are described, inter alia, in GenBank Accession numbers P02671, P02675, and P02679. In another embodiment, the fibrinogen is any other fibrinogen known in the art. Each possibility represents a separate embodiment of the present invention.

In another embodiment, the $T_m$ of a structural protein of a composition of the present invention falls within a range of melting temperatures particularly suitable for compositions of the present invention. In another embodiment, the structural protein has a $T_m$ under 400° C. Each possibility represents a separate embodiment of the present invention.

Oils and Oil Coatings

The solid particulate phase of compositions of the present invention is surrounded by, immersed in, embedded in, dispersed in or suspended in an oil carrier. Typically, the oil phase, in addition to coating the solid phase, impregnates the solid phase, which is composed of the nanoparticles, biopolymer, and pharmacologically active molecule. Reference to an "oil," "oil layer," "oil phase," or "oil coating" does not preclude the presence of an additional component or components useful in methods of the present invention (e.g. a fat-soluble co-factor or anti-oxidant). Rather, the term indicates that the oil, oil layer, oil phase, or coating is composed primarily of a pharmaceutically acceptable oil carrier, in which the other components are mixed and/or dissolved. The oil carrier can be composed of either one or a plurality of types of oils, as described further herein. In another embodiment, the coating consists essentially of lipids and/or oils. In another embodiment, the coating of the composition comprises a pharmaceutically acceptable oil carrier. In another embodiment, the oil carrier is a naturally-occurring oil. In another embodiment, the oil is a mixture of natural vegetable oils. In another embodiment, the oil carrier is sesame oil. In another embodiment, the oil carrier is olive oil. In another embodiment, the oil carrier is linseed oil. In another embodiment, the oil carrier is evening primrose oil. In another embodiment, the oil carrier is silicone oil. In another embodiment, the oil carrier is sea buckthorn oil. In another embodiment, the oil carrier is selected from the group consisting of sesame oil, olive oil, linseed oil, evening primrose oil, silicone oil, and sea buckthorn oil. In another embodiment, the oil carrier includes, but is not limited to, an oil selected from the group consisting of sunflower oil, corn oil, soybean oil, jojoba oil, marrow oil, grapeseed oil, hazelnut oil, apricot oil, macadamia oil and castor oil.

In another embodiment, the oil carrier is of animal origin, such as lanolin.

In another embodiment, the oil carrier is a synthetic oil. In another embodiment, the oil carrier is a fatty alcohol. In certain preferred embodiments, the oil carrier is 2-octyldodecanol. In certain other preferred embodiments, the oil carrier is selected from the group consisting of a fatty acid ester and a phenylsilicone. In certain more preferred embodiments, the oil carrier is selected from the group consisting of a phenyl-trimethicone, a diphynyldimethicone, and a poly-methylphenylsiloxane.

In another embodiment, the oil carrier is another suitable oil known in the art. Each possibility represents a separate embodiment of the present invention.

In another embodiment, the oil consists essentially of naturally-occurring lipids and/or oils. Each possibility represents a separate embodiment of the present invention.

"Plurality of oils" refers, in another embodiment, to two or more oils. In another embodiment, a composition of the present invention comprises three or more oils. In another embodiment, a composition of the present invention comprises four or more oils. In another embodiment, a composition of the present invention comprises more than four oils. In another embodiment, the oil phase comprises a mixture of oils selected from natural vegetable oils. Each possibility represents a separate embodiment of the present invention.

In another embodiment, an oil component of the present invention comprises a component capable of stimulating secretion of bile salts or bile acids when ingested by a subject. In another embodiment, the bile-stimulating component is an oil. In another embodiment, the component is olive oil or an extract thereof. In another embodiment, the component is any other bile salt/acid stimulating lipid-soluble substance known in the art. In another embodiment, the carrier is the bile salt/acid stimulating substance. In another embodiment, the bile salt/acid stimulating substance is a substance separate from the carrier. Each possibility represents a separate embodiment of the present invention.

In another embodiment, an oil component of the present invention contains a significant quantity of one or more anti-oxidants. For example, sea buckthorn (oblepicha) oil contains a significant quantity of beta-carotene. In another embodiment, any other oil enriched in one or more anti-oxidants may be used. Each possibility represents a separate embodiment of the present invention.

In another embodiment, the oil components of the compositions of the present invention may include an oil with a relatively high melting temperature. According to some embodiments an oil component of the present invention comprises a component that has a melting temperature ($T_m$) of at least 5-10° C. In another embodiment, the high $T_m$ component is a liquid at room temperature. In another embodiment, the oil carrier is the high $T_m$ component. In another embodiment, the high-$T_m$ component is included in addition to another oil carrier. A non-limiting example of a high-$T_m$ oil is jojoba oil. In another embodiment, the high $T_m$ oil is any other high melting temperature oil known in the art. In another embodiment, the high $T_m$ oil is used as the majority of the oil carrier in the matrix carrier of the present invention. Each possibility represents a separate embodiment of the present invention.

In another embodiment, a matrix composition of the present invention further comprises an additional oil component. As provided herein, mixing of multiple oil components of compositions of the present invention according to the methods disclosed herein provides self-ordering or self-organization of matrix structure, due to competitive adsorption and minimization of the free energy. The term "additional oil component" encompasses an oil or mixture of oils, as described elsewhere herein. In another embodiment, the oil carrier of the additional oil component is olive oil. In another embodiment, the oil carrier is another suitable oil known in the art. In another embodiment, the additional oil component comprises an antioxidant. Each possibility represents a separate embodiment of the present invention.

In another embodiment, the biologically active protein or peptide is included in the additional oil or mixture of oils, instead of in the first-added oil or mixture of oils. In another embodiment, the biologically active protein or peptide is combined with an antioxidant and oil (the first-added or additional oil or mixture of oils) prior to adding to the solid phase. Each possibility represents a separate embodiment of the present invention.

In another embodiment, the additional oil, oil or mixture of oils has a higher viscosity than the first-added oil or mixture of oils. In another embodiment, without wishing to be bound by any theory or mechanism of action, the use of a higher viscosity oil or oil mixture at this stage enables self-ordering or self-organization of structure due to competitive adsorption and minimization of the free energy. Each possibility represents a separate embodiment of the present invention.

In another embodiment, a matrix composition of the present invention further comprises a third oil or mixture of oils. In another embodiment, the third oil component comprises an antioxidant. In another embodiment, the third oil component is sesame oil. In another embodiment, the third oil component is another suitable oil known in the art. In another embodiment, the third oil, oil or mixture of oils has a higher viscosity than the additional oil or mixture of oils. Each possibility represents a separate embodiment of the present invention.

In another embodiment, a highly penetrative oil carrier is included in the outer oil or mixture of oils. Non-limiting examples of highly penetrative oils are sesame oil, tea tree (Melaleuca) oil, lavender oil, almond oil, and grape seed oil. In another embodiment, the highly penetrative oil carrier promotes efficient transport of the substances into the blood. Each possibility represents a separate embodiment of the present invention.

In another embodiment, a matrix composition or pharmaceutical composition of the present invention further comprises a pharmaceutically acceptable wax. The term "wax" means a lipophilic compound, which is solid at room temperature (25° C.), with a reversible solid/liquid change of state, having a melting point of greater than or equal to 30° C., which may be up to 120° C. By bringing the wax to the liquid state (melting), it is possible to render it miscible with any oils present and to form a microscopically homogeneous mixture, but on returning the temperature of the mixture to room temperature, recrystallization of the wax in the oils of the mixture is obtained. The wax may be a natural wax, for example bees wax, a wax derived from plant material, or a synthetic wax prepared by esterification of a fatty acid and a long chain alcohol. Other suitable waxes include petroleum waxes such as a paraffin wax. In another embodiment, the wax stabilizes the matrix carrier composition. In another embodiment, the inclusion of wax facilitates formation of a tablet containing the matrix carrier composition. Each possibility represents a separate embodiment of the present invention.

Pharmaceutical Compositions

In another embodiment, the present invention provides a pharmaceutical composition comprising: (a) pharmacologically inert nanoparticles having a hydrophobic surface, wherein the size of the nanoparticles is between 1-100 nanometers, in intimate non-covalent association with a biopolymer comprising a polysaccharide; and (b) a biologically active protein or peptide non-covalently attached to the nanoparticles and the biopolymer; wherein the matrix formed by the nanoparticles, biopolymer, and biologically active protein or peptide is embedded, dispersed, immersed or suspended in oil. In another embodiment, the biologically active protein or peptide is non-covalently attached to the hydrophobic surfaces of the nanoparticles and the hydrophilic surfaces of the biopolymer. In another embodiment, the biologically active protein or peptide is also non-covalently attached to hydrophobic surfaces of the biopolymer. In another embodiment, the particle size of the pharmaceutical composition following its formation, but prior to ingestion is between 100-500,000 nm. In another embodiment, the particle size is between 100-50,000 nm. In another embodiment, the particle size is between 100-5000 nm. Each possibility represents a separate embodiment of the present invention.

Various components of pharmaceutical compositions of the present invention, namely nanoparticles, biopolymers, and oils, are described hereinabove. In another embodiment, the oil phase of the matrix carrier composition comprises a plurality of oils. In another embodiment, the combined weight of the particulate matter containing: nanoparticles, the biopolymer, and the protein or peptide is not more than 25% of the overall weight of the composition. Each possibility represents a separate embodiment of the present invention.

In another embodiment, the matrix-carrier composition is held together by non-covalent forces. In another embodiment, without wishing to be bound by any theory or mechanism of action, the non-covalent forces between the components of the matrix composition enable the matrix composition to self assemble when the components are mixed together, as described herein. In another embodiment, the non-covalent forces cause the nanoparticles, biopolymer, and protein/polypeptide to form an intimate mixture. In another embodiment, the matrix composition exhibits an ordered, fractal structure. Each possibility represents a separate embodiment of the present invention.

In another embodiment, the nanoparticle-biopolymer-protein/peptide complex is dispersed within the oil phase of the matrix composition. In another embodiment, the oil phase is impregnated with the nanoparticle-biopolymer-protein/peptide complex of the matrix composition. As provided herein, the present invention provides compositions wherein the nanoparticles, biopolymer, and protein or peptide form a matrix that is impregnated and completely surrounded by the oil phase. Each possibility represents a separate embodiment of the present invention.

Proteins and Polypeptides Suitable as Active Agents in Compositions of the Present Invention "Protein or peptide having therapeutic activity," as used herein, refers to a protein or peptide that exhibits activity that may be therapeutic in a subject in need thereof. In certain preferred embodiments, the term encompasses proteins and peptides known to be exhibit biological activity generally, not limited to their formulation in compositions of the present invention. In another embodiment, the biologically active protein or peptide is a glycoprotein or glycosylated protein. In another embodiment, the protein or peptide is non-glycosylated. In another embodiment, the protein or peptide is any other type of protein or peptide known in the art. Each possibility represents a separate embodiment of the present invention.

The molecular weight (MW) of the biologically active protein or peptide is, in another embodiment, under 100 kilodaltons (kDa). In another embodiment, the MW is under 90 kDa. In another embodiment, the MW is under 80 kDa. In another embodiment, the MW is under 70 kDa. In another embodiment, the MW is under 60 kDa. In another embodiment, the MW is under 50 kDa. In another embodiment, the MW is under 45 kDa. In another embodiment, the MW is under 40 kDa. In another embodiment, the MW is under 35 kDa. In another embodiment, the MW is under 30 kDa. In another embodiment, the MW is under 25 kDa. In another embodiment, the MW is under 20 kDa. Each possibility represents a separate embodiment of the present invention.

In another embodiment, the MW of the biologically active protein or peptide is over 100 kDa. In another embodiment, the MW is 100-5000 kDa. In another embodiment, the MW is 100-4000 kDa. In another embodiment, the MW is 100-3000 kDa. In another embodiment, the MW is 100-2000 kDa. In another embodiment, the MW is 100-1500 kDa. In another embodiment, the MW is 100-1000 kDa. In another embodiment, the MW is 100-800 kDa. In another embodiment, the MW is 100-700 kDa. In another embodiment, the MW is 100-600 kDa. In another embodiment, the MW is 100-500 kDa. In another embodiment, the MW is 100-400 kDa. In another embodiment, the MW is 100-300 kDa. In another embodiment, the MW is 100-200 kDa. In another embodiment, the MW is 100-150 kDa. In another embodiment, the biologically active protein or peptide is a synthetic polymer of unknown or variable MW. Each possibility represents a separate embodiment of the present invention.

As provided herein, biologically active proteins and peptides of a variety of molecular weights can be successfully incorporated into matrix carrier compositions of the present invention. For example, insulin (MW 5,808); Ribonuclease (MW 14,000); and deoxyribonuclease (MW more than 30,000 daltons) have been utilized.

In another embodiment, the biologically active protein or peptide is selected from the group consisting of a growth factor, a cytokine, a peptide hormone, an analgesic peptide, an enzyme, a small peptide, a blood coagulating factor peptide, and a peptide neurotransmitter. In another embodiment, the biologically active protein or peptide is a synthetic polymer. In another embodiment, the protein or peptide is any other type of biologically active protein or peptide known in the art. Each possibility represents a separate embodiment of the present invention.

In another embodiment, the biologically active protein or peptide is a growth factor. Non-limiting examples of growth factors are platelet-derived growth factor (PDGF), stem cell growth factor (SCF), hepatocyte growth factor (HGF), transforming growth factor (TGF), nerve growth factor (NGF), epidermal growth factor (EGF), fibroblast growth factor (FGF), and insulin-like growth factor (IGF). In another embodiment, the growth factor is any other type of growth factor known in the art. Each possibility represents a separate embodiment of the present invention.

In another embodiment, the biologically active protein or peptide is a cytokine. Non-limiting examples of cytokines are tumor necrosis factor, interferon, and interleukin. In another embodiment, the cytokine is any other type of cytokine known in the art. Each possibility represents a separate embodiment of the present invention.

In another embodiment, the biologically active protein or peptide is a hematopoietic factor. Non-limiting examples of hematopoietic factors are erythropoietin, granulocyte colony-stimulating factor, granulocyte-macrophage colony-stimulating factor, macrophage colony-stimulating factor and thrombopoietin. In another embodiment, the hematopoietic factor is any other type of hematopoietic factor known in the art. Each possibility represents a separate embodiment of the present invention.

In another embodiment, the biologically active peptide is a peptide hormone. Non-limiting examples of peptide hormones are luteinizing hormone-releasing hormone (LH-RH), thyrotropin-releasing hormone (TRH), somatostatin, pituitary growth hormone, prolactin, adrenocorticotropic hormone (ACTH), melanocyte-stimulating hormone (MSH), thyroid-stimulating hormone (TSH), luteinizing hormone (LH), follicle-stimulating hormone (FSH), vasopressin, oxytoxin, calcitonin, parathyroid hormone (PTH), glucagon, gastrin, secretin, pancreozymin, cholecystokinin, angiotensin, human placenta lactogen, human chorionic gonadotropin (HCG), cerulean, motilin, glucose-dependent insulinotropic polypeptide (GIP), and glucagon-like peptide-1 (GLP-1). In another embodiment, the peptide hormone is any other type of peptide hormone known in the art. Each possibility represents a separate embodiment of the present invention.

In another embodiment, the biologically active peptide is an analgesic peptide. Non-limiting examples of analgesic peptides are enkephalin, endorphin, dynorphin, kyotorphin. In another embodiment, the analgesic peptide is any other type of analgesic peptide known in the art. Each possibility represents a separate embodiment of the present invention.

In another embodiment, the biologically active protein is an enzyme. As provided herein, compositions of the present invention enable enzymes to be administered while retaining a significant fraction of their catalytic activity. Non-limiting examples of enzymes are DNase, RNase, superoxide dismutase (SOD), urokinase, tissue plasminogen activator (TPA), asparaginase, kallikrein, and pyruvate dehydrogenase. In another embodiment, the enzyme is any other type of enzyme known in the art. Each possibility represents a separate embodiment of the present invention.

In another embodiment, the biologically active peptide is a neurotransmitter. Non-limiting examples of peptide neurotransmitters are bombesin, neutrotensin, bradykinin, and substance P. In another embodiment, the neurotransmitter is any other type of neurotransmitter known in the art. Each possibility represents a separate embodiment of the present invention.

In another embodiment, the biologically active protein or peptide is an anti-coagulant peptide.

In another embodiment, the biologically active peptide is an antibody. In another embodiment, the antibody is a monoclonal antibody. In another embodiment, the antibody is an anti-tumor necrosis factor (TNF) antibody. Anti-TNF antibodies are commercially available and include Infliximab™, Etanercept™, and Adalimumab™. In another embodiment, the antibody is any other anti-TNF antibody known in the art. In another embodiment, the antibody is against carcinoembryonic antigen (CEA). In another embodiment, the antibody is against ovarian carcinoma antigen CA125. In another embodiment, the antibody is any other antibody having therapeutic activity known in the art. Each possibility represents a separate embodiment of the present invention.

In another embodiment, the biologically active peptide is an antibody fragment. In another embodiment, the antibody fragment is an Fc fragment. In another embodiment, the antibody fragment is a Fab fragment. In another embodiment, the antibody fragment is a light chain. In another embodiment, the antibody fragment is a heavy chain. In another embodiment, the antibody fragment is any other type of antibody fragment known in the art. In another embodiment, the antibody fragment is a fragment of an anti-TNF antibody. In another embodiment, the antibody fragment is a fragment of any other antibody having therapeutic activity known in the art. Each possibility represents a separate embodiment of the present invention.

In another embodiment, the biologically active peptide is an antibody conjugated to a pharmaceutical agent. In another embodiment, the pharmaceutical agent is a cytokine. In another embodiment, the pharmaceutical agent is a dominant-negative tumor necrosis factor (TNF) protein. In another embodiment, the pharmaceutical agent is tumor necrosis factor (TNF) protein. In another embodiment, the pharmaceutical agent is a radioactive isotope. In another embodiment, the pharmaceutical agent is any other pharmaceutical agent known in the art. In another embodiment, the antibody-pharmaceutical agent conjugate exhibits activity against viral infection. In another embodiment, the antibody-pharmaceutical agent conjugate exhibits activity against bacterial infection. Each possibility represents a separate embodiment of the present invention.

In another embodiment, the biologically active peptide is an antibody fragment conjugated to a pharmaceutical agent.

In another embodiment, the biologically active peptide is selected from the group consisting of calcitonin, erythropoietin, pituitary growth hormone, a dominant-negative tumor necrosis factor (TNF) protein, interferon-alpha, interferon-beta, interferon-gamma, and an anti-tumor necrosis factor (TNF) antibody.

In another embodiment, the biologically active protein or peptide is a DNase. The term includes endodeoxyribonucleases and exodeoxyribonucleases. DNases are phosphodiesterases capable of hydrolyzing polydeoxyribonucleic acid into individual 3' or 5'-phosphate deoxynucleotides on hydrolysis of deoxyribonucleic acid (DNA). Non-limiting examples of DNase are DNase I, DNase II, and proteins with sequences set forth in GenBank Accession Numbers YP_001911052, CAA62587, Q8WZ79, and NP_650672. In another embodiment, the DNase is any other DNase known in the art. Each possibility represents a separate embodiment of the present invention.

In another embodiment, the biologically active protein or peptide is an RNase. The term includes endoribonucleases and exoribonucleases. RNases are enzymes capable of degrading poly-RNA. Non-limiting examples of RNases are RNase A, RNase H, RNase I, RNase III, RNase L, RNase P, RNase PhyM, RNase T1, RNase T2, RNase U2, RNase V1, RNase V, PNPase, RNase PH, RNaseII, RNase R, RNase D, RNase T, oligoribonuclease, exoribonuclease I, and exoribonuclease II. In another embodiment, RNase is administered together with an anti-oxidant. Each possibility represents a separate embodiment of the present invention.

In another embodiment, the biologically active protein or peptide is pituitary growth hormone. Pituitary growth hormone is a polypeptide hormone, typically 191-amino acids in length, secreted by the human adenohypophysis (anterior pituitary gland), and is also known as GH or somatotropin. The sequences of non-limiting examples of pituitary growth hormones are set forth in GenBank Accession numbers NM_000515, NM_022559, NM_022560, NM_022561, and NM_022562. In another embodiment, the pituitary growth hormone is any other pituitary growth hormone known in the art. Each possibility represents a separate embodiment of the present invention.

In another embodiment, the biologically active protein or peptide is Copaxone™. Copolymer 1 (Cop 1), also known as Copaxone™ and glatiramer acetate, is a drug for the treatment of multiple sclerosis. It consists of a synthetic polymer of L-alanine, L-lysine, L-glutamic acid and L-tyrosine with an average molar fraction of 0.141, 0.427, 0.095, and 0.338, respectively and an average molecular weight of 5,000-9,000 daltons. In addition to Copolymer 1, Copaxone™ contains 40 mg/ml of mannitol, which increases BBB permeability. Copaxone™ is well known in the art, and is described, for example, in Jacobs L. et al. (Advances in specific therapy for multiple sclerosis. *Curr. Opin. Neurol.* 7:250-4, 1994). In another embodiment, the composition of the present invention comprises Copaxone™ as the biologically active polypeptide and further comprises mannitol. Each possibility represents a separate embodiment of the present invention.

Figure 14:
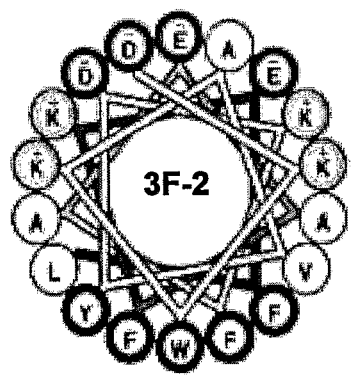
FIG. 14: Helical wheel representation of the apolipoprotein A-1 mimetic peptides 3F-2 and 3F-14 The wheel is projected along the axis of the helix from the N to the C terminus with the hydrophobic side facing downward. The primary structure is given above each wheel diagram. The amino acid composition of both peptides is the same. The sequence is different. The plus and minus signs denote the charges on the amino acids at neutral pH. The bold black denotes aromatic residues.
Figure 14:
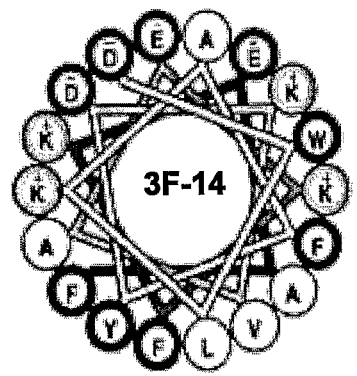

In another embodiment, the biologically active protein or peptide is an apolipoprotein A-1 mimetic peptide. Apolipoprotein A-1 mimetic peptides are well known in the art, and are described, for example, in Ou J. et al. (L-4F, an apolipoprotein A-1 mimetic, dramatically improves vasodilation in hypercholesterolemia and sickle cell disease. *Circulation*, 107:2337-41, 2003). A non-limiting example of an apolipoprotein A-1 mimetic peptide is L-4F. Structures of additional apolipoprotein A-1 mimetic peptide are depicted in FIG. 14. In another embodiment, the apolipoprotein A-1 mimetic peptide is any other apolipoprotein A-1 mimetic peptide known in the art. Each apolipoprotein A-1 mimetic peptide represents a separate embodiment of the present invention.

In another embodiment, the biologically active protein or peptide is rituximab. Rituximab (Rituxan®) is a therapy that selectively targets CD20-positive B-cells. Use of rituximab is well known in the art, and is described, for example, in Ramos-Casals M. et al. (A systematic review of the off-label use of biological therapies in systemic autoimmune diseases. *Medicine (Baltimore)*. 87:345-64, 2008).

In another embodiment, the biologically active protein or peptide is calcitonin. Non-limiting examples of calcitonin peptides are set forth in GenBank Accession numbers NM_001741, NM_001033953, and NM_001033952. In another embodiment, the calcitonin is any other calcitonin known in the art. In another embodiment, calcitonin-containing compositions are used to treat osteoporosis. Each possibility represents a separate embodiment of the present invention.

In another embodiment, the biologically active protein or peptide is an erythropoietin. The sequences of non-limiting examples of erythropoietin peptides are set forth in GenBank Accession numbers NM_000799 and AM933611. Other non-limiting examples of erythropoietin is epoetin alpha, which is available commercially as Eprex™, Epogen™, and Procrit™; Recormon™ (epoetin beta); Aranesp™ (darbepoetin alpha); and Mircera™ (methoxy polyethylene glycol-epoetin beta). In another embodiment, the erythropoietin is any other erythropoietin known in the art. Each possibility represents a separate embodiment of the present invention.

In another embodiment, the biologically active protein or peptide is an interferon-alpha. The sequences of non-limiting examples of interferon-alpha proteins are set forth in GenBank Accession numbers NM_024013, NM_000605, NM_002170, NM_002173, NM_021057, NM_002175, NM_021268, NM_002172, NM_006900, NM_002171, NM_021002, NM_002169, NM_021068. In another embodiment, the interferon-alpha is any other interferon-alpha known in the art. Each possibility represents a separate embodiment of the present invention.

In another embodiment, the biologically active protein or peptide is an interferon-beta. The sequences of non-limiting examples of interferon-beta proteins are set forth in GenBank Accession numbers NM_002176, DJ418445, and AL390882. In another embodiment, the interferon-beta is any other interferon-beta known in the art. Each possibility represents a separate embodiment of the present invention.

In another embodiment, the biologically active protein or peptide is an interferon-gamma. The sequences of non-limiting examples of interferon-gamma proteins are set forth in GenBank Accession numbers NM_000619, BC070256, V00543, and X13274. In another embodiment, the interferon-gamma is any other interferon-gamma known in the art. Each possibility represents a separate embodiment of the present invention.

In another embodiment, the biologically active protein or peptide is a urease. The sequences of non-limiting examples of urease proteins are set forth in GenBank Accession numbers AF468788 and M65260. In another embodiment, the urease is any other urease known in the art. Each possibility represents a separate embodiment of the present invention.

In another embodiment, the biologically active protein or peptide is a catalase. The sequences of non-limiting examples of catalase proteins are set forth in GenBank Accession numbers NM_001752 and NM_012520. In another embodiment, the catalase is any other catalase known in the art. Each possibility represents a separate embodiment of the present invention.

In another embodiment, the biologically active polypeptide is a peptidomimetic, or small protein-like chain designed to mimic a peptide.

In another embodiment, "peptidomimetic" refers to a peptide containing a non-naturally occurring amino acid or amino acid analog. In another embodiment, the amino acid analog is a D or L residue having the following formula: NH—CHR—CO, wherein R is an aliphatic group, a substituted aliphatic group, a benzyl group, a substituted benzyl group, an aromatic group or a substituted aromatic group and wherein R does not correspond to the side chain of a naturally occurring amino acid. This term also refers to the D-amino acid counterpart of naturally occurring amino acids. Amino acid analogs are well known in the art; a large number of these analogs are commercially available. In another embodiment, use of non-naturally occurring amino acids in the peptide has the advantage that the peptide is more resistant to degradation by enzymes which fail to recognize them.

Alternatively, a functional group may be added to the side chain, deleted from the side chain or exchanged with another functional group. Examples of non-conservative substitutions of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine. In yet another alternative, the side chain of the substituting amino acid can have significantly different steric and electronic properties from the functional group of the amino acid being substituted. Examples of such modifications include tryptophan for glycine, lysine for aspartic acid and —$(CH_2)_4$COOH for the side chain of serine.

An amino acid analogue can be substituted for amino acid residues in the compounds of this invention both as conservative and as non-conservative substitutions. These peptidomimetic organic moieties either replace amino acid residues of essential and non-essential amino acids or act as spacer groups within the peptides in lieu of deleted amino acids (of non-essential amino acids). The peptidomimetic organic moieties often have steric, electronic or configurational properties similar to the replaced amino acid and such peptidomimetics are used to replace amino acids in the essential positions, and are considered conservative substitutions. However, such similarities are not necessarily required. The only restriction on the use of peptidomimetics is that the peptides retain their therapeutic properties. Peptidomimetics can be produced by organic synthetic techniques. Examples of suitable peptidomimetics include D amino acids of the corresponding L amino acids; tetrazol; isosteres of amide bonds; an LL 3 amino 2 propenidone 6 carboxylic acid. Further suitable peptidomimetics include hydroxyl-1,2,3,4-tetrahydroisoquinoline-3-carboxylate; 1,2,3,4 tetrahydroisoquinoline-3-carboxylate; histidine isoquinolone carboxylic acid (HIC); (2S, 3S) methyl phenylalanine, (2S, 3R) methyl phenylalanine, and (2R, 3S) methyl phenylalanine and (2R, 3R) methyl phenylalanine.

The above examples of peptidomimetics are not meant to be limiting. Each possibility represents a separate embodiment of the present invention.

Additional Components

In another embodiment, a composition of the present invention further comprises an antioxidant. In another embodiment, the antioxidant is a pharmaceutically acceptable antioxidant. In another embodiment, the antioxidant is selected from the group consisting of vitamin E, superoxide dismutase (SOD), omega-3, and beta-carotene. Each possibility represents a separate embodiment of the present invention.

In another embodiment, the composition further comprises an enhancer of the biologically active protein or peptide. In another embodiment, the composition further comprises a cofactor of the biologically active protein or peptide. Each possibility represents a separate embodiment of the present invention.

In another embodiment, a composition of the present invention further comprises pharmaceutical-grade surfactant. Surfactants are well known in the art, and are described, inter alia, in the *Handbook of Pharmaceutical Excipients* (eds. Raymond C Rowe, Paul J Sheskey, and Sian C Owen, copyright Pharmaceutical Press, 2005). In another embodiment, the surfactant is any other surfactant known in the art. Each possibility represents a separate embodiment of the present invention.

In another embodiment, a composition of the present invention further comprises pharmaceutical-grade emulsifier or emulgator (emollient). Emulsifiers and emulgators are well known in the art, and are described, inter alia, in the *Handbook of Pharmaceutical Excipients* (ibid). Non-limiting examples of emulsifiers and emulgators are eumulgin, Eumulgin B1 PH, Eumulgin B2 PH, hydrogenated castor oil cetostearyl alcohol, and cetyl alcohol. In another embodiment, the emulsifier or emulgator is any other emulsifier or emulgator known in the art. Each possibility represents a separate embodiment of the present invention.

In another embodiment, a composition of the present invention further comprises pharmaceutical-grade stabilizer. Stabilizers are well known in the art, and are described, inter alia, in the *Handbook of Pharmaceutical Excipients* (ibid). In another embodiment, the stabilizer is any other stabilizer known in the art. Each possibility represents a separate embodiment of the present invention.

In another embodiment, a composition of the present invention further comprises an amino acid selected from the group consisting of arginine, lysine, aspartate, glutamate, and histidine. In another embodiment, analogues and modified versions of arginine, lysine, aspartate, glutamate and histidine are included in the terms "arginine," "lysine," "aspartate", "glutamate" and "histidine," respectively. In another embodiment, the amino acid provides additional protection of ribonuclease or other active molecules. In another embodiment, the amino acid promotes interaction of biologically active protein or peptide with a target cell. In another embodiment, the amino acid is contained in an oil component of the composition. Each possibility represents a separate embodiment of the present invention.

In another embodiment, a composition of the present invention further comprises one or more pharmaceutically acceptable excipients, into which the matrix carrier composition is mixed. In another embodiment, the excipients include one or more additional polysaccharides. In another embodiment, the excipients include one or more waxes. In another embodiment, the excipients provide a desired taste to the composition. In another embodiment, the excipients influence the drug consistency, and the final dosage form such as a gel capsule or a hard gelatin capsule.

Non limiting examples of excipients include: Antifoaming agents (dimethicone, simethicone); Antimicrobial preservatives (benzalkonium chloride, benzelthonium chloride, butylparaben, cetylpyridinium chloride, chlorobutanol, chlorocresol, cresol, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Chelating agents (edetate disodium, ethylenediaminetetraacetic acid and salts, edetic acid); Coating agents (sodium carboxymethyl-cellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Humectants (glycerin, hexylene glycol, propylene glycol, sorbitol); Polymers (e.g., cellulose acetate, alkyl celluloses, hydroxyalkylcelluloses, acrylic polymers and copolymers); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); This list is not meant to be exclusive, but instead merely representative of the classes of excipients and the particular excipients which may be used in oral dosage compositions of the present invention. Each possibility represents a separate embodiment of the present invention.

In another embodiment, the weight of the particulate matter of the composition of the present invention is not more than 33% of the weight of the oil phase. In the case of a matrix carrier not containing an active compound, the particulate matter is composed of the nanoparticles and the biopolymer. In the case of a matrix carrier pharmaceutical composition, the particulate matter is composed of the nanoparticles, the biopolymer, and the active compound. The weight of the oil phase is the weight of the oil carrier plus additional oils mixed therewith and substances dissolved therein, if any, for all the oil components combined. In another embodiment, the weight of the particulate matter is not more than 30% of the weight of the oil phase. In another embodiment, the weight of the particulate matter is not more than 25% of the weight of the oil phase. In another embodiment, the weight of the particulate matter is not more than 20% of the weight of the oil phase. In another embodiment, the weight of the particulate matter is not more than 15% of the weight of the oil phase. In another embodiment, the weight of the particulate matter is not more than 10% of the weight of the oil phase. In another embodiment, the weight of the particulate matter is not more than 8% of the weight of the oil phase. In another embodiment, the weight of the particulate matter is not more than 5% of the weight of the oil phase. Each possibility represents a separate embodiment of the present invention.

In another embodiment, the weight of particulate matter is not more than 75% of the total weight of the composition. In another embodiment, the weight of particulate matter is not more than 50% of the total weight of the composition. In another embodiment, the weight of the particulate matter is not more than 30% of the total weight of the composition. In another embodiment, the weight of the particulate matter is not more than 25% of the total weight of the composition. In another embodiment, the weight of the particulate matter is not more than 20% of the total weight of the composition. In another embodiment, the weight of the particulate matter is not more than 15% of the total weight of the composition. In another embodiment, the weight of the particulate matter is not more than 10% of the total weight of the composition. In another embodiment, the weight of the particulate matter is not more than 8% of the total weight of the composition. In another embodiment, the weight of the particulate matter is not more than 6% of the total weight of the composition. In another embodiment, the weight of the particulate matter is not more than 5% of the total weight of the composition. Each possibility represents a separate embodiment of the present invention.

Methods of Administration

In another embodiment, the present invention provides a method of administering a biologically active protein or peptide to a subject in need thereof, comprising orally administering to the subject a pharmaceutical composition of the present invention, thereby administering a biologically active protein or peptide to a subject.

In another embodiment, the biologically active protein or peptide is DNase. In another embodiment, the biologically active protein or peptide is RNase. In another embodiment, the biologically active protein or peptide is calcitonin. In another embodiment, the biologically active protein or peptide is erythropoietin. In another embodiment, the biologically active protein or peptide is selected from the group consisting of calcitonin, erythropoietin, pituitary growth hormone, a dominant-negative tumor necrosis factor (TNF) protein, tumor necrosis factor (TNF) protein, interferon-alpha, interferon-beta, and interferon-gamma. In another embodiment, the biologically active protein or peptide is any other biologically active protein or peptide known in the art. Each possibility represents a separate embodiment of the present invention.

The size, properties, and classification of the biologically active protein or peptide may be any of those described herein. Each possibility represents a separate embodiment of the present invention.

Formulation Methods

In another embodiment, the present invention provides a method of manufacturing a matrix carrier composition, the method comprising the steps of: (a) dry blending nanoparticles having a hydrophobic surface, wherein the size of the nanoparticles is between 1-100 nanometers, with a biopolymer comprising a polysaccharide, whereby the nanoparticles form an intimate non-covalent association with the biopolymer; and (b) blending the nanoparticles and biopolymer into an oil. Preferably, the nanoparticles and biopolymer form a complex. In another embodiment, the complex is embedded, dispersed, immersed or suspended in the oil. In another embodiment, the particle size of the matrix carrier composition is between 100-500,000 nanometers. In another embodiment, the particle size of the matrix carrier composition is between 100-50,000 nanometers. In another embodiment, the particle size is between 100-5000 nm. Each possibility represents a separate embodiment of the present invention. Formulation methods of the present invention encompass embodiments wherein additional components are present in step (a). In another embodiment, more than one type of biopolymer is present together with the nanoparticles. In another embodiment, a branched polysaccharide and a dietary fiber are present together with the nanoparticles. In another embodiment, a branched polysaccharide and a linear polysaccharide are present together with the nanoparticles. In another embodiment, a branched biopolymer, a linear polysaccharide, and an insoluble fiber are present together with the nanoparticles.

In another embodiment, the method of manufacturing the matrix carrier composition, comprises the step of: blending silica nanoparticles having a hydrophobic surface and a biopolymer comprising a polysaccharide and a high molecular weight structural protein into an oil, whereby the nanoparticles form an intimate non-covalent association with the biopolymer.

In another embodiment, the present invention provides a method of manufacturing a pharmaceutical composition, the method comprising the steps of: (a) dry blending pharmacologically inert nanoparticles having a hydrophobic surface, wherein the size of the nanoparticles is between 1-100 nanometers, with a biopolymer comprising a polysaccharide, whereby the nanoparticles form an intimate non-covalent association with the biopolymer; (b) dissolving a biologically active protein or peptide into an oil; and (c) blending the nanoparticles and biopolymer into the oil, wherein the nanoparticles, biopolymer, and protein or peptide are embedded, dispersed, immersed or suspended in the oil. Preferably, the nanoparticles, biopolymer, and protein or peptide form a complex. In another embodiment, the complex is embedded, dispersed, immersed or suspended in the oil. In another embodiment, the biologically active protein or peptide is attached to the hydrophobic surfaces of the nanoparticles and the hydrophilic surfaces of the biopolymer via non-covalent forces. In another embodiment, the particle size of the matrix carrier composition is between 100-50,000 nanometers. In another embodiment, the particle size is between 100-5,000 nm. Each possibility represents a separate embodiment of the present invention.

In another embodiment, step (b) of the above method comprises the step of directly dissolving a lyophilized protein or peptide into the oil or oil mixture. In another embodiment, a solution of the biologically active protein or peptide is mixed with the oil or oil mixture and the aqueous phase can then be removed. Each possibility represents a separate embodiment of the present invention.

In another embodiment, the biologically active protein or peptide forms a suspension when mixed with the oil or oil mixture. In another embodiment, the biologically active protein or peptide is dissolved in the oil or oil mixture. As provided herein, charged proteins and peptides that would be expected to have low solubility in oil, such as Copaxone, are able to be incorporated into oil-containing matrix compositions of the present invention. Without wishing to be bound by any theory or mechanism of action, this may be a consequence of adsorption of the peptides onto the solid phase of compositions of the present invention. The adsorption is likely to be mediated by interaction of the hydrophobic regions of the peptide with the nanoparticle surface, while the hydrophilic regions of the peptide interact with hydrophilic regions of polysaccharide, each via non-covalent forces. In another embodiment, the protein or peptide is mixed with the oil in the presence of an alcohol. In another embodiment, polyethylene glycol is present. In another embodiment the polyethylene glycol has a molecular weight in the 200-8000 dalton range. In another embodiment the protein or peptide is mixed with the oil in the presence of perfluorocarbon. In another embodiment the perfluorocarbon is a liquid at room temperature. Each possibility represents a separate embodiment of the present invention.

In another embodiment, the protein or peptide is mixed with the oil under anhydrous conditions. In another embodiment, moisture is present. In another embodiment, an aqueous solution of the protein or peptide is mixed with the oil. Each possibility represents a separate embodiment of the present invention.

The properties and classification of the nanoparticles, biopolymer, and biologically active protein or peptide of the above methods may be any of those described herein. Each possibility represents a separate embodiment of the present invention. "Oil" as referred to in methods of the present invention can refer to either a single oil, a mixture of oils, or an oil phase. As described herein, a mixture of oils or oil phase will typically comprise an oil carrier. In another embodiment, the mixture of oils or oil phase further comprises an additional oil or oils or an additional component or components. Each possibility represents a separate embodiment of the present invention.

In another embodiment, step (a) of a formulation method of the present invention further comprises the step of confirming that the nanoparticles and biopolymer are properly homogenized. In another embodiment, any of the following three tests are utilized: (a) the mixture appears homogenous; (b) the volume of the mixture is smaller than the sum of volumes of the 2 components; and (c) the mixture does not sink when placed on the surface of a still body of water. Each possibility represents a separate embodiment of the present invention.

The step of dry mixing is, in another embodiment, performed using a high shear mixer. In another embodiment, the step of mixing is performed using a high-speed mixer. In another embodiment, the step of mixing is performed using any other means suitable for generating a homogenous solid phase from nanoparticles and a biopolymer. Each possibility represents a separate embodiment of the present invention.

In another embodiment, a formulation method of the present invention further comprises the step of adding an additional oil following the addition of the first-added oil or mixture of oils. The term "additional oil" encompasses an oil or mixture of oils, as described elsewhere herein. In another embodiment, the additional oil component comprises an antioxidant. Each possibility represents a separate embodiment of the present invention.

In another embodiment, the biologically active protein or peptide is included in the additional oil or mixture of oils, instead of in the first-added oil or mixture of oils.

In another embodiment, the additional oil, oil or mixture of oils has a higher viscosity than the first-added oil or mixture of oils. In another embodiment, without wishing to be bound by any theory or mechanism of action, the use of a higher viscosity oil or oil mixture at this stage enables formation of ordered structures in the composition.

In another embodiment, a method of the present invention further comprises the step of adding a third oil or mixture of oils after addition of the above-described additional oil or mixture of oils. In another embodiment, the third oil component comprises an antioxidant. Each possibility represents a separate embodiment of the present invention.

In another embodiment, a formulation method of the present invention further comprises the step of adding a pharmaceutically acceptable wax following the addition of the first-added oil or mixture of oils. In another embodiment, the wax is a substance with properties similar to beeswax. In another embodiment, the wax is a substance having the following properties: (a) plastic (malleable) at normal ambient temperature; (b) having a melting point above approximately 45° C. (113° F.); (c) a low viscosity when melted, relative to a typical plastics; (d) insoluble in water; and (e) hydrophobic. In certain preferred embodiments, the wax is beeswax. In another embodiment, the wax stabilizes the matrix carrier composition. In another embodiment, the inclusion of wax facilitates formation of a tablet containing the matrix carrier composition. Each possibility represents a separate embodiment of the present invention.

In another embodiment, the wax is heated as part of a method of the present invention. In another embodiment, the wax is pulverized. In another embodiment, the wax is both heated and pulverized. In another embodiment, the heating and/or pulverization are performed prior to blending with the other components. In another embodiment, the wax remains hot while blending with the other components is begun. In another embodiment, the heating and/or pulverization are performed during blending with the other components. In another embodiment, the heating and/or pulverization are performed both prior to and during blending with the other components. Each possibility represents a separate embodiment of the present invention.

In another embodiment, a highly penetrative oil carrier is included in the outer oil or mixture of oils. In another embodiment, the highly penetrative oil carrier promotes efficient transport of the substances into the blood. Each possibility represents a separate embodiment of the present invention.

In another embodiment, a formulation method of the present invention further comprises the step of including an amino acid in an oil or mixture of oils. In another embodiment, the amino acid is included in the last-added oil or mixture of oils. In another embodiment, the amino acid is a charged amino acid. In another embodiment, the amino acid is selected from the group consisting of arginine, lysine, and derivatives thereof. In another embodiment, an antioxidant, enhancer, or cofactor is included. Each possibility represents a separate embodiment of the present invention.

As provided herein, methods have been developed to formulate a variety of biologically active proteins and peptides in orally administrable form. In certain preferred embodiments, the components are mixed in a particular order in order to produce a suspension of matrix carrier compositions that protect the active ingredient from digestive processes in the stomach. Without wishing to be bound by any theory of mechanism of action, the biopolymer, particularly when branched, absorbs hydraulic and mechanical stresses experienced during digestion. The oil coating constitutes a physical barrier that provides additional protection against digestive enzymes.

Figure 2:
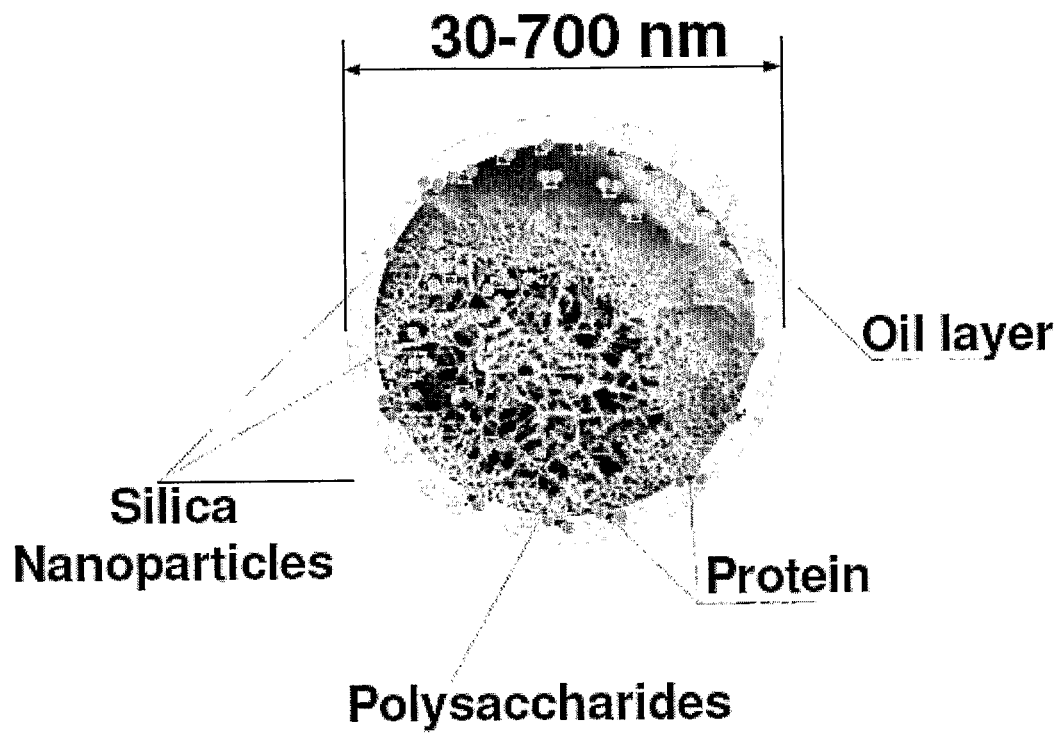
FIG. 2: Schematic view of the structure formed in the small intestine due to joint action of hydrodynamic and enzymatic processes.

Without wishing to be bound by any theory or mechanism of action, the secretion of bile acids causes dispersion of the oil suspension into smaller particles, which can be absorbed in the small intestine. The size of the nanoparticles influences the extent of dispersion of the solid phase within the oil, due to the unique structure of matrix carriers of the present invention. While the particle size is reduced after traversing the stomach and entering the small intestine, the particles remain within a size range of 30-1000 nm, too large to be substrate for lipases and peptidases, preserving the protective effect of the composition. In certain preferred embodiments, the particles remain within a size range of 30-700 nm after traversing the stomach and entering the small intestine (FIG. 2). Advantageously, lipid-coating particles of this size are absorbed in a similar way to chylomicrons by lacteal vessels, which are lymphatic vessels originating in the villi of the small intestine. Particles absorbed in this manner can reach the bloodstream without undergoing first-pass metabolism, largely preserving the biological activity of the active agent.

The following formulas and information provide guidance to those skilled in the art for practicing the present invention:

The relative amounts of nanoparticles and biopolymer are calculated according to the following equation:

$$V^1_{SF} * Eb^I_{SF} * (1 \pm 0.3) = V^{II}_{SF} * Eb^{II}_{SF}.$$

In the above equation:
  $V^1_{SF}$ and $V^{II}_{SF}$ are the volumes of the nanoparticles and biopolymer, respectively.
  $Eb^I_{SF}$ is the molecular bond energy of the nanoparticles (typically more than 3 eV).
  $Eb^{II}_{SF}$ is the energy of the lowest molecular or hydrogen bond in the biopolymer.

Figure 3A:
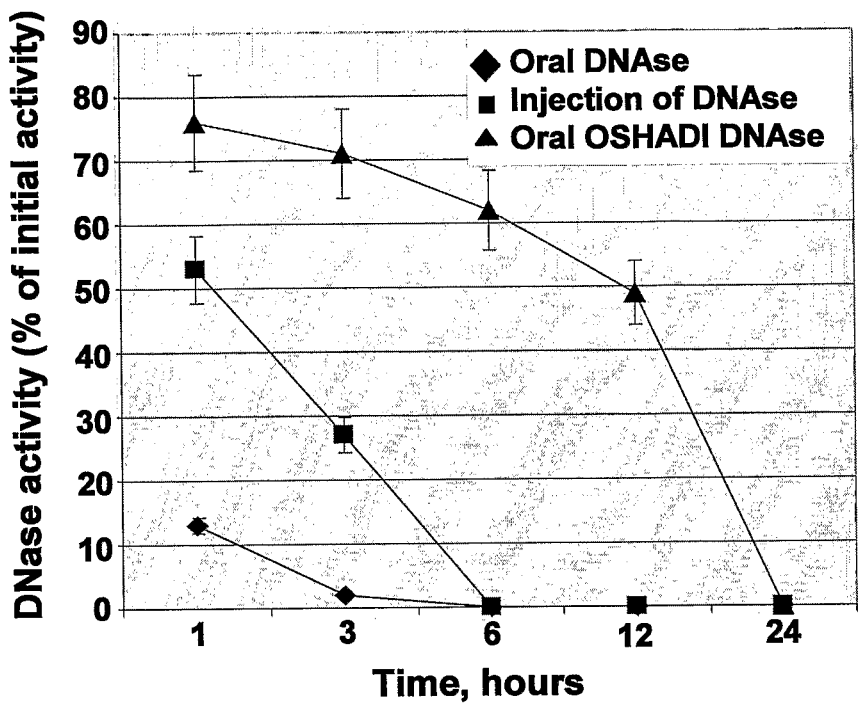
FIG. 3: A. DNase activity in mouse plasma following oral administration of a fast-release DNase matrix composition. B. DNase activity in human plasma following oral administration of 75 mg of a DNase oral composition of the present invention. Each line represents a different subject before (the first point) and after intake of the DNase oral composition.

Matrix carriers for any protein or peptide of interest can be designed using the following principles:
1. The required concentration of the active agent in the final formulation is determined, based on previous experience, pharmacokinetics and pharmacodynamics.
2. Based on the above, the molar concentration of the active substance and total surface area of the nanoparticles and biopolymer are estimated.
3. The absorption area of the active substance is estimated, based on the active substance's molecular weight and three-dimensional structure. In the case of a globular molecule, the absorption area is 30-40% of the molecule's spherical surface. In the case of an elongated molecule, the absorption area is estimated to be the same as an area of a single strip with the length of molecule and the width of the widest molecule's molecular branch. Other molecules are estimated as a combination of both geometries.
4. The thickness of the protective oil layer is estimated based on the three-dimensional structure of the active molecule. It should be at least 10 times the diameter of a globular molecule or the maximal branch size of an elongated molecule. The thickness of the oil coating of matrix carriers of the present invention is determined by the following properties of the oil or mixture of oils: (a) the viscosity and melting temperature; (b) the acidity; and (c) the concentration of polar groups.
5. The estimated area of the nanoparticles necessary for the formation of the matrix carrier of the present invention is calculated. The area should be at least 10 times higher than the active substance's estimated absorption area as determined in step 3.
6. The estimated area of the biopolymer necessary for the formation of the matrix carrier of the present invention is calculated. The area should be at least 10 times higher than that of the nanoparticles as determined in step 5.
7. The first oil into which the active molecule is added is chosen, preferably an oil having a relatively low viscosity and low concentration of polar groups. Suitable examples are evening primrose oil, sesame oil, and silicon oil.
8. Inserting both solid phases into this oil leads to adsorption of the nanoparticles onto the surface of the biopolymer. This preserves the integrity of the protective oil layer.
9. A second oil component is added. The second oil is chosen based on its viscosity, which is commensurate with the desired rate of release of the active molecule from the matrix carrier.
10. A third oil component is added in order to improve the interaction between the active molecule and its target and further protect the active molecule from deg Results A comparison between the in vivo DNase activity of a fast-release DNase composition of the present invention (also called oral Oshadi DNase), injected DNase and orally administered DNase. While 50% of the initial DNase activity of the oral Oshadi DNase was retained after 12 hours, no activity was detected after only 6 hours for both injected and orally administered DNase. (FIG. 3A).

Figure 3B:
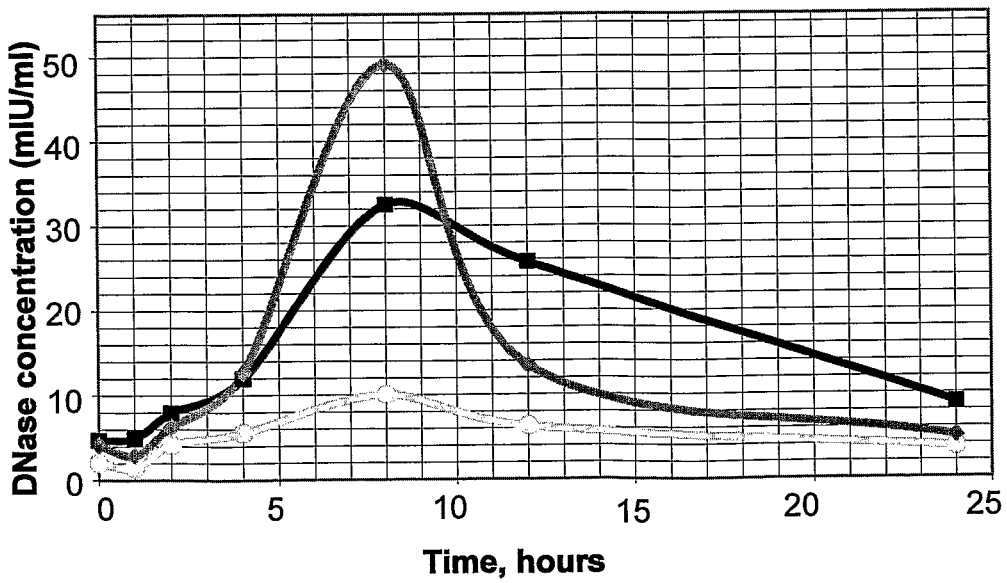

In another experiment, 75 mg of the above-described medium-term DNase matrix carrier oral composition was administered to human subjects, and serum DNase activity was measured. Potent activity was observed in all subjects at 4, 8, and 12 hours after administration (FIG. 3B).

In another experiment, 20 mg/day of the above-described medium-term DNase matrix carrier composition was administered orally to 4 human subjects for one week, and the concentration of free DNA in serum was measured in each subject independently. All subjects exhibited a decline in free DNA concentration in blood serum (Table 1).

TABLE 1

Comparison of free DNA concentration in human serum before and after treatment with DNase.

| Subject | Free DNA before the treatment, μgr/ml | Free DNA after the treatment, μgr/ml |
| --- | --- | --- |
| #1 | 170.07 | 136.33 |
| #2 | 292.31 | 180.91 |
| #3 | 189.42 | 130.71 |
| #4 | 214.03 | 197.43 |

The above Examples show that the release rate of matrix compositions of the present invention can be readily modulated as desired according to the needs of the subject and the therapeutic agent.

Example 4

Preparation of RNase Matrix Carrier Composition (RNase Formulation I)

12 g Ambrotose™ rice polysaccharides were weighed with an analytical scale, combined with 4 g hydrophobic silica R972, and mixed by vortexing at 900 rpm for 5 min. Association between the Ambrotose™ and the silica was determined by the mixture's ability to float after being placed on the surface of a water-filled beaker. 120 ml linseed oil and 60 ml sea buckthorn (Oblepicha) oil were combined in a beaker and stirred for 2 minutes at 100 rpm with a magnetic stirrer. 8 g RNase were weighed with an analytical scale and stirred into the oil mixture at 20 rpm for 1 min, then at 50 rpm for 3 min. The Ambrotose™/silica mixture was than added to the oil-RNase solution and stirred for 20 minutes at 50 rpm. 60 ml olive oil was than added, and the mixture was stirred at 50 rpm for 4 min. 10 tablets of "Plus" Dried Amino Acids (L-Glutamic Acid, Glycine, L-Lysine, L-Arginine; from Mannatech Inc, Coppell, Tex. 75019, USA) were pulverized, sifted to remove debris, then stirred into the mixture at 20 rpm for 30 min. The volume was brought up to 400 ml with sesame oil, and the mixture was stirred at 50 rpm for 5 min. The product was stored refrigerated (3-8° C.).

In some experiments, the product is packaged into gelatin enteric covering capsules.

Example 5

In Vivo Release Profile of RNase Matrix Carrier composition

RNase activity was measured using the Samson-Med Bio-Assay as follows: 30 μl of serum were incubated for 10 min with 1 mg yeast RNA. Reduction in RNA concentration was observed and measured photometrically.

Results

Figure 4:
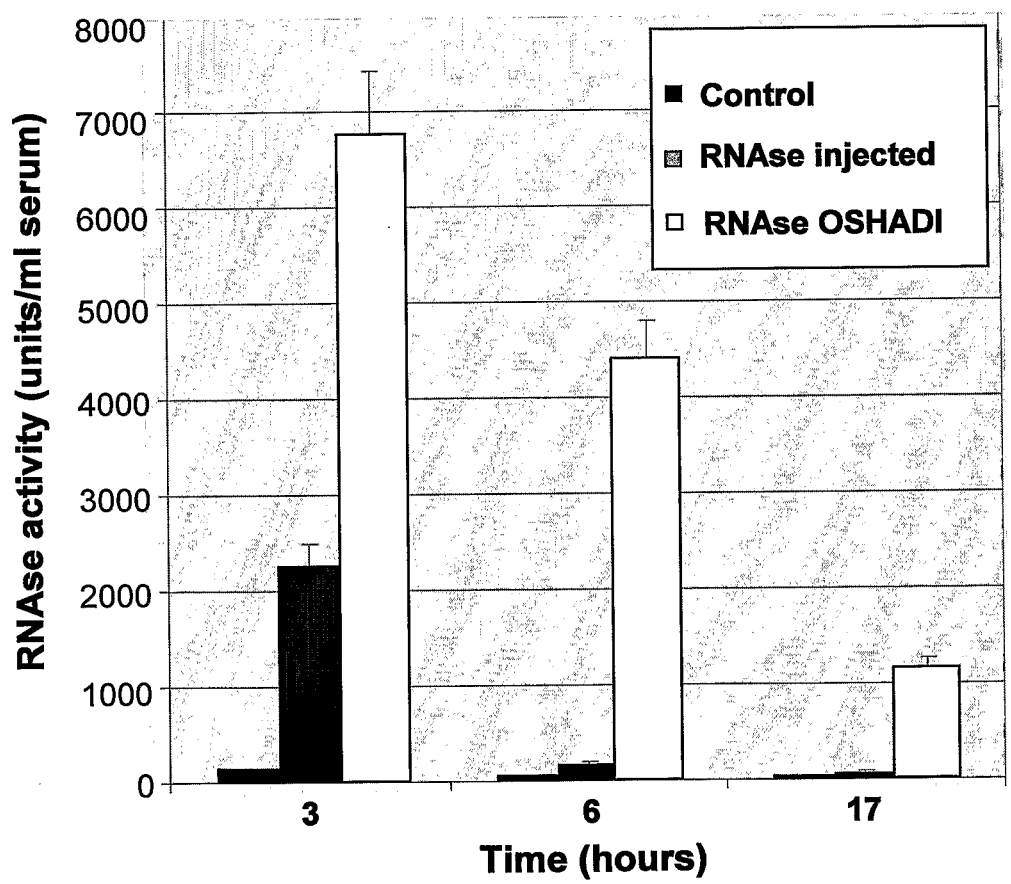
FIG. 4: RNase activity in mouse plasma following injection of RNase or oral administration of RNase matrix compositions. First bar in each series: orally administered RNase. Second bar in each series: injected RNase. Third bar in each series: RNase oral composition of the present invention.

A comparison between the in vivo RNase activity of administered RNase matrix carrier composition (formulation III—example 4) (also called oral Oshadi RNase), injected RNase and orally administered RNase (control). The RNase activity was measured 3, 6 and 17 hours after administration of the RNase. While the formulation continued to impart RNase activity for the entire time tested (17 hours), the activity of the injected RNase reached background RNase levels after only 6 hours. In addition, the maximal RNase activity at the time points tested was 3-fold higher in the RNase matrix carrier composition than injected RNase. Orally administered RNase conferred no detectable activity (FIG. 4).

Example 6

Preparation of Insulin Matrix Carrier Compositions

Actrapid™ matrix carrier composition (Formulation V) was produced, using the following ingredients:
Olive oil, 11 ml
Benefiber™, 3 g
Insulin Actrapid™, 9 ml
Oblepicha oil, 9 ml
Hydrophobic silica R972, 1.2 g
Sesame Oil up to 75 ml.

Benefiber™ (Novartis Nutrition GmbH, Germany) and silica were placed into a beaker and mixed by vortexing at 900 rpm for 5 min. Association between the Benefiber™ and the silica was determined by the mixture's ability to float after being placed on the surface of a water-filled beaker. Actrapid™ insulin was added and stirred for 15 minutes at 50 rpm. Sesame oil and sea buckthorn (oblepicha) oil were combined in a beaker and vortexed on a low setting for 15 minutes. Olive oil was added to the oils and stirred with a glass rod. The solid phase mixture and oil mixture were combined and mixed at 100 rpm with a magnetic stirrer. The volume was brought up to 75 ml with sesame oil and stirred with a glass rod. In animal experiments, the composition was administered by gavage. The product contained 12 IU/ml insulin and was packaged into gelatin enteric covering capsules.

An additional insulin matrix carrier composition (Formulation VI) was prepared using NovoRapid™ insulin, using the above protocol. In this case NovoRapid™ insulin was used instead of Actrapid™ insulin.

An additional Actrapid™ formulation (Formulation II) using the following ingredients was designed for short-term insulin release:
Insulin Actrapid™, 1 ml
Olive oil, 1.5 ml.
Ambrotose™, 0.7 g.
Silica R972, 0.1 g
Oblepicha oil, 1.5 ml
Evening primrose oil, up to 5 ml 0.7 g rice polysaccharides (Ambrotose™, Mannatech Inc, Coppell, Tex. 75019, USA) was combined with 0.1 g hydrophobic silica fumed R972 (Degussa Inc), and mixed by vortexing at 900 rpm for 5 min. Association between the Ambrotose™ and the silica was determined by the mixture's ability to float after being placed on the surface of a water-filled beaker. 1 ml Actrapid™ insulin was added and stirred for 15 minutes at 50 rpm. 1.5 ml olive oil was added and stirred for 2 minutes at 100 rpm with a magnetic stirrer. Sea buckthorn (oblepicha) oil was added and stirred for 2 minutes at 100 rpm with a magnetic stirrer. The volume was brought up to 5 ml with evening primrose oil and stirred at 50 rpm for 20 min. The product was stored refrigerated (3-8° C.). In a separate preparation, the amount of the ingredients was doubled, yielding identical results.

The final insulin concentration was 20 IU/ml. For human administration, the product was packaged into gelatin enteric covering.

Figure 5A:
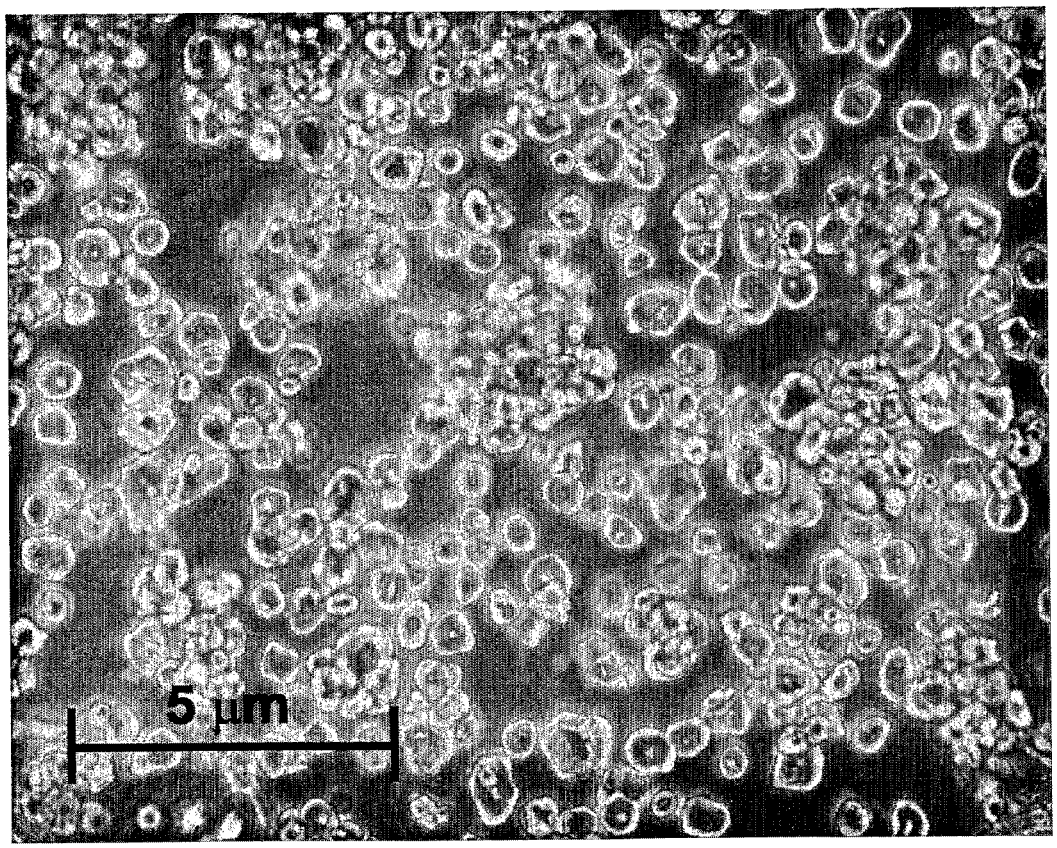
FIG. 5: A. Light microscopy picture of insulin matrix carrier Formulation IV (example 6). B. Effect of oral administration of Actrapid™ insulin oral compositions of the present invention on Blood Glucose Level (BGL) in diabetic (STZ-treated) mice. Different symbols represent individual mice.

An additional insulin matrix carrier composition (Formulation IV) was prepared using BIOCON insulin, using the following protocol and the ingredients set forth in Table 2, using methods similar to those set forth in previous Examples. A light microscopy picture of the composition is shown in FIG. 5A.

1. Mix oblepicha+olive oil+⅓ of sesame oil.
2. Add Insugen™ insulin powder (BIOCON) into the mixture of oils and mix.
3. Mix fiber+chitin+amylopectin+silica
4. Add the mixture of step 3 to the mixture of oils and insulin of step 2 and mix.
5. Add the rest of the sesame oil and mix.

TABLE 2

Ingredients for the preparation of the BIOCON matrix carrier composition.

Formulation IV

| Insulin Powder (BIOCON), mg | 36.4 | 109.2 | 182 |
|---|---|---|---|
| Olive Oil, ml | 33 | 33 | 33 |
| Sea Buckthorn Oil (Oblepicha), ml | 42 | 42 | 42 |
| Seasame Oil, ml | up to 100 | up to 100 | up to 100 |
| Amylopectin, g | 11.25 | 11.25 | 11.25 |
| Chitin, g | 1.9 | 1.9 | 1.9 |
| Silica R972, g | 2.5 | 2.5 | 2.5 |
| Final concentration of insulin, IU/ml | 10 | 30 | 50 |

Example 7

Efficacy of the Oral Insulin Composition of the Present Invention in Diabetic Mice:

Materials and Experimental Methods

Diabetes was induced by streptozotocin in male adult BALB/c mice (7-10 weeks old), weight 23-28 gr. Control mice were matched for age and weight.

Streptozotocin (STZ)-induced diabetes treatment: Diabetes was induced by 2 injections of 500 and 700 µl of 1.5 mg/ml streptozotocin, separated by 48 hours, in male adult BALB/c mice (7-10 weeks old), of an average weight of 23-28 gr. Untreated mice of approximately the same age and weight were used as control. Blood glucose levels (BGL) were assessed 48 hours after STZ injection by a standard FreeStyle™ glucometer (Abbot Diabetes Cere Inc, Alameda, Calif.) from the tail vein blood samples.

Insulin compositions were administered orally to mice by gavage (1 ml volume), without prior deprivation of food or water. During the experiment mice were supplied with food and water as usual.

Compositions: The first experiment utilized Formulations V and VI described in Example 6. The second experiment utilized Formulation IV described in Example 6.

Blood insulin concentration. Blood insulin concentrations were detected by ELISA (Human Insulin ELISA kit, Linco).

Treatment Groups:
1. Control group 1: no STZ treatment, no insulin administration.
2. Control group 2: no STZ treatment, oral insulin composition of the present invention administered by gavage.
3. Control group 3: STZ treated, no insulin administration.
4. Diabetic (STZ treated) mice; insulin administered by SC injection.
5. Diabetic (STZ treated) mice; insulin was administered by gavage.
6. Diabetic (STZ treated) mice; insulin was administered using the oral insulin composition of the present invention by gavage.
7. Diabetic (STZ treated) mice; matrix carrier (without insulin) administered by gavage a control.

Results

Figure 5B:
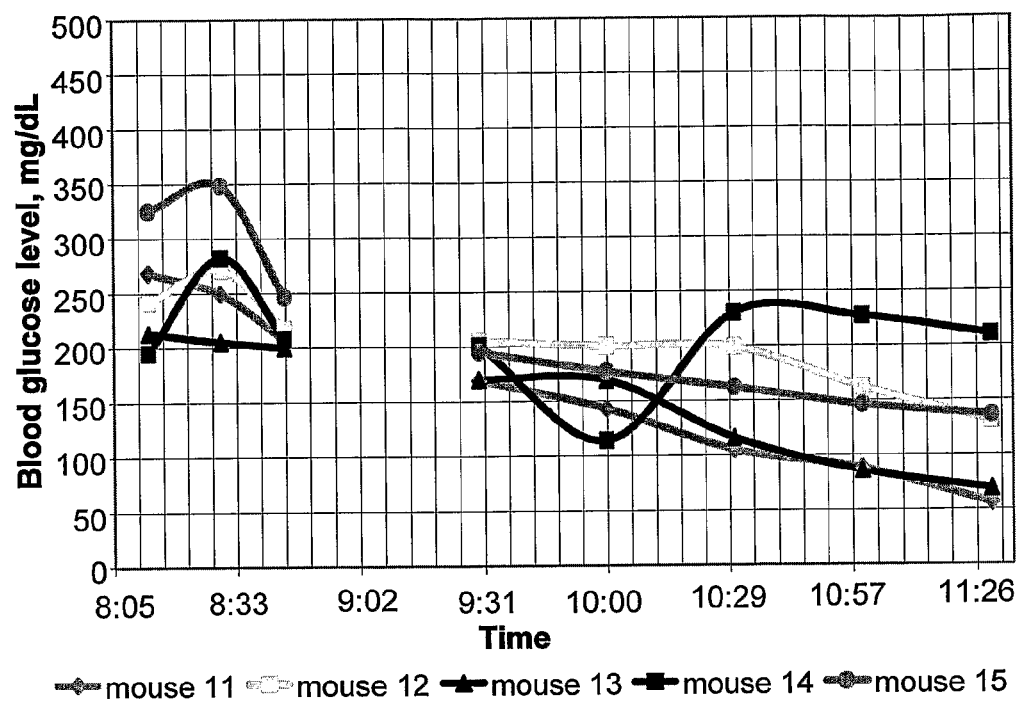
Figure 6:
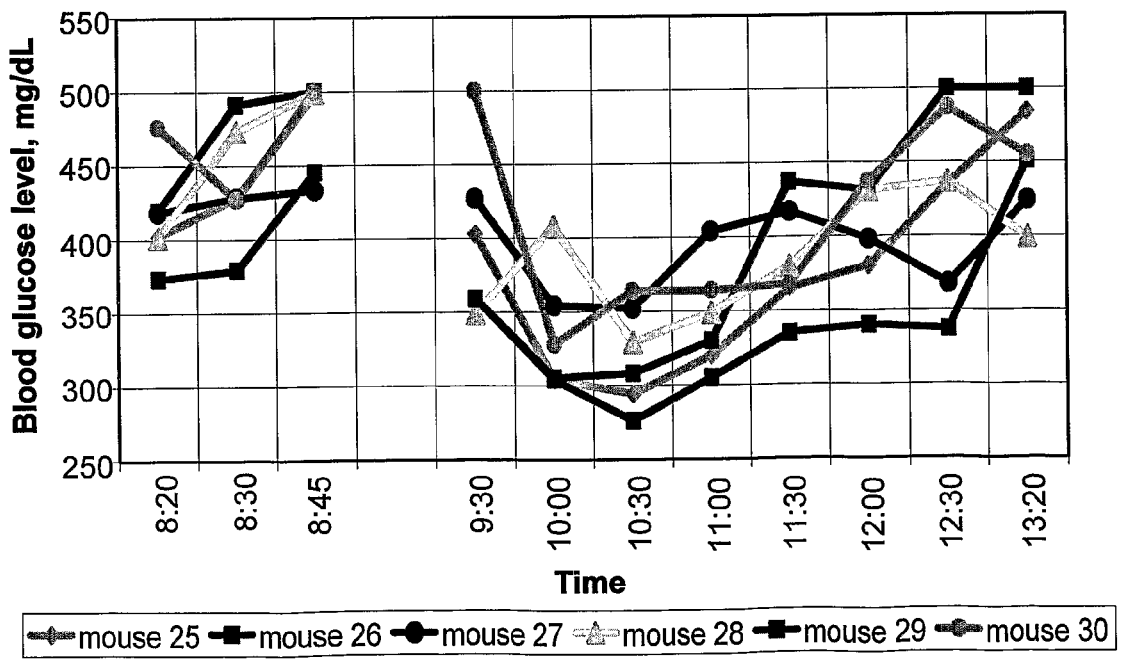
FIG. 6: Effect of oral administration of NovoRapid™ insulin oral compositions of the present invention on BGL in diabetic (STZ-treated) mice. Different symbols represent individual mice.
Figure 7:
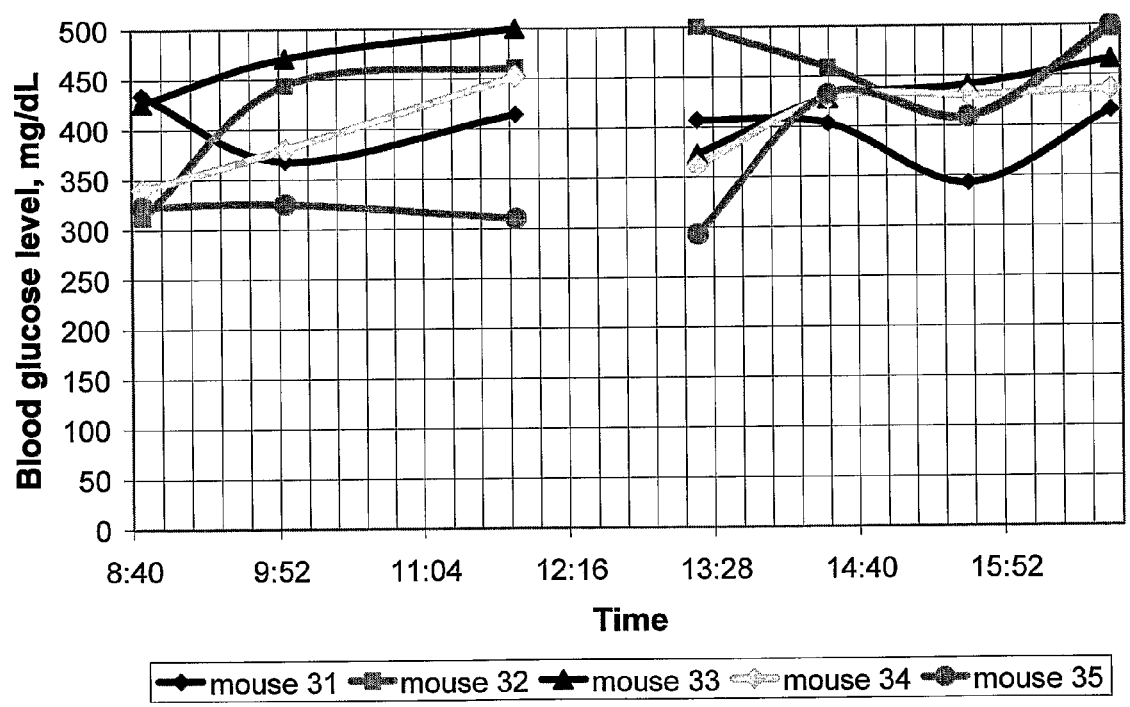
FIG. 7: BGL levels in STZ-treated mice following administration of 25 IU Insulin (by BIOCON) in PBS (gavage). Different symbols represent individual mice.

In a first experiment, diabetes was induced by streptozotocin (STZ) in male adult BALB/c mice, followed by administration of Actrapid™—(12 IU) and NovoRapid™—(9.5 IU) based insulin compositions (Formulation V and Formulation VI) of the present invention. Both compositions significantly reduced blood glucose levels (FIGS. 5B and 6, respectively). By contrast, STZ-treated mice that received empty matrix carrier compositions (lacking insulin), orally administered Actrapid™ or NovoRapid™ insulin, or were given 25 IU Insulin (BIOCON) in PBS (gavage) (FIG. 7) did not exhibit significant reduction in blood glucose levels. Normal mice (not STZ-treated) that received insulin compositions exhibited no significant reduction in blood glucose level. Normal and diabetic mice injected with insulin, by contrast, exhibited hypoglycemia symptoms that were in some cases fatal.

Figure 8A:
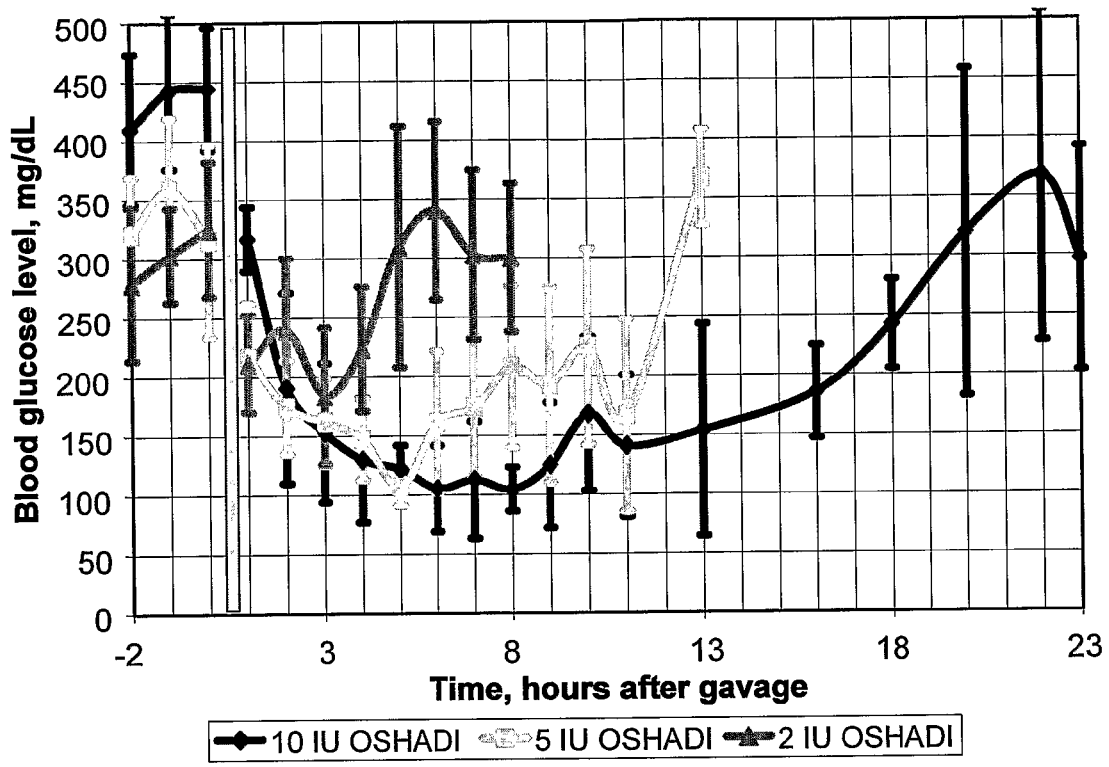
FIG. 8: A. Dose response curve towards the insulin oral compositions of the present invention. (Mean blood glucose concentrations based on at least 5 mice). B-D: Data from individual mice at 2 (B), 5 (C), and 10 (D) IU. E. Effect of SC-injected insulin on STZ mice. F. Effect of 12 IU of insulin composition on normal mice. Break in figures B-J indicates time of administration. Horizontal axis: time. Vertical axis: mean BGL level, mg/dL, ranging from 0-500 (A-E) or 0-160 (F). Different symbols represent individual mice. G,H,I. Comparison of 10 (G), 5 (H), or 2 (I) IU insulin oral composition of the present invention vs. injection of the same amount of insulin.
Figure 8B:
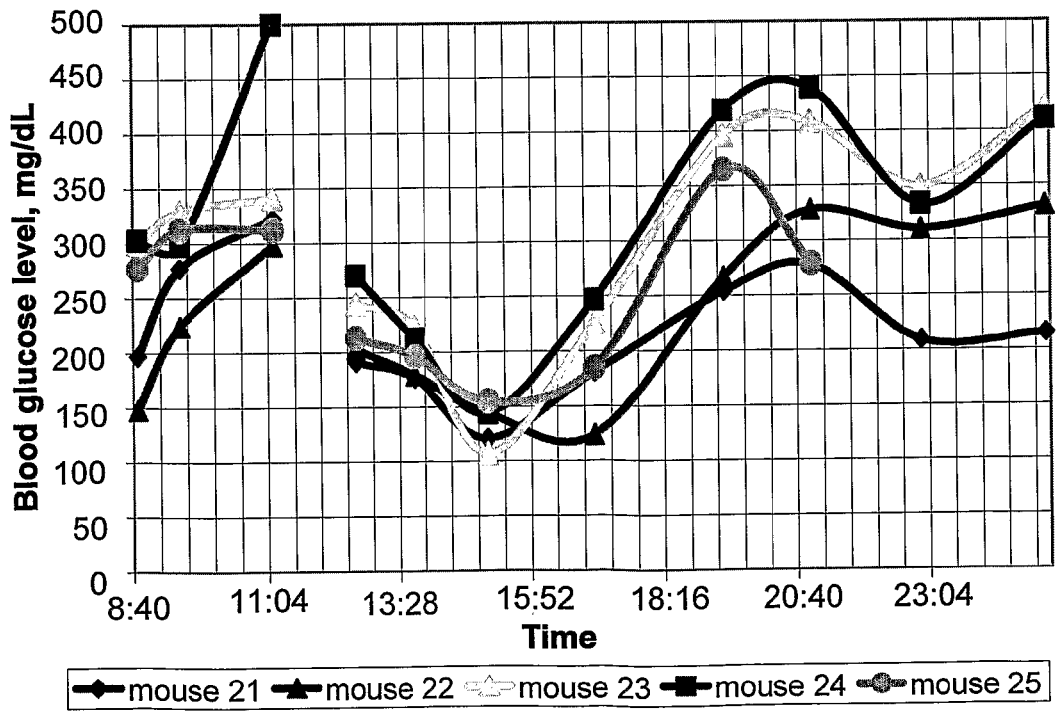
Figure 8C:
Figure 8D:
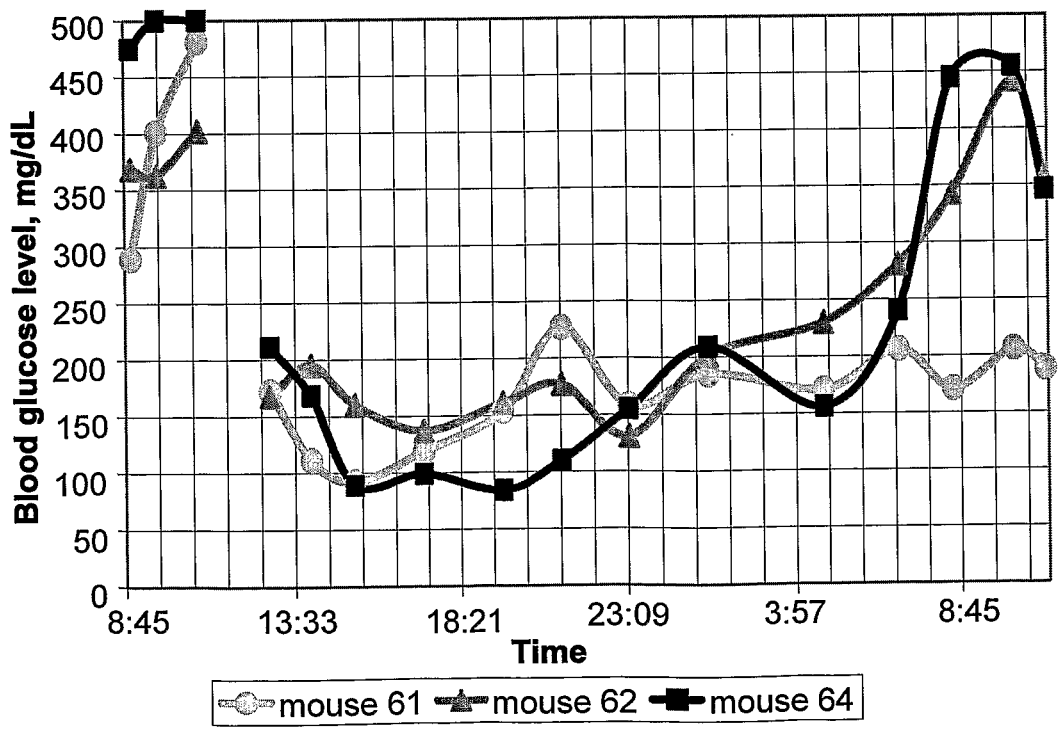
Figure 8E:
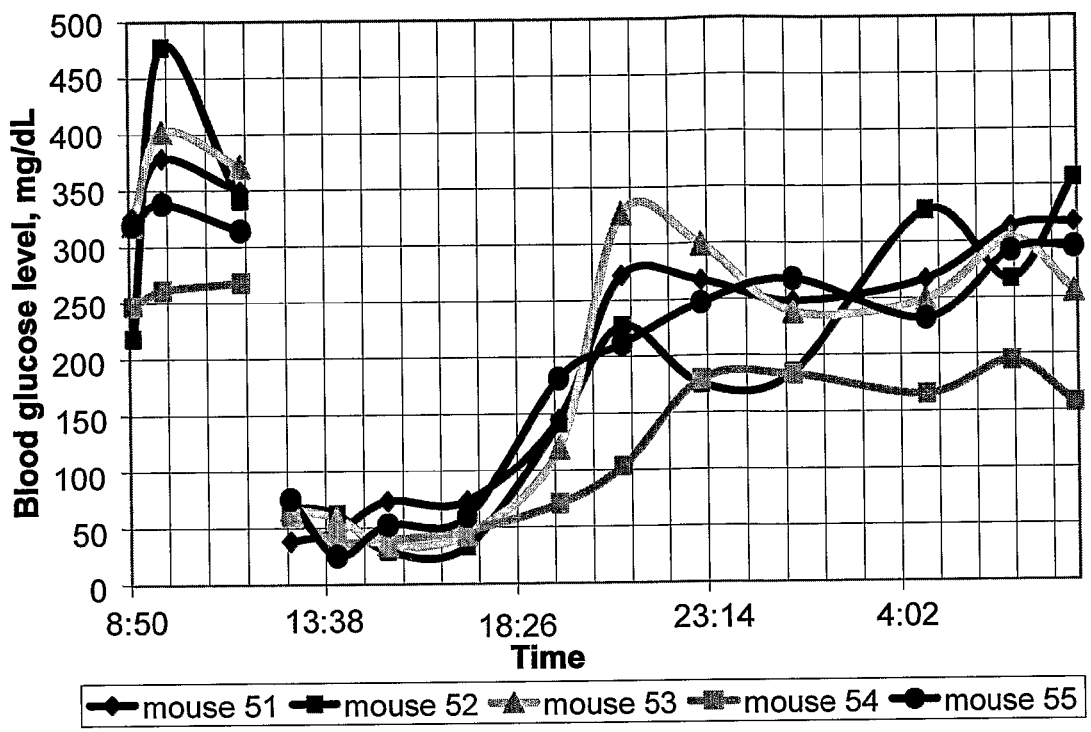
Figure 8F:
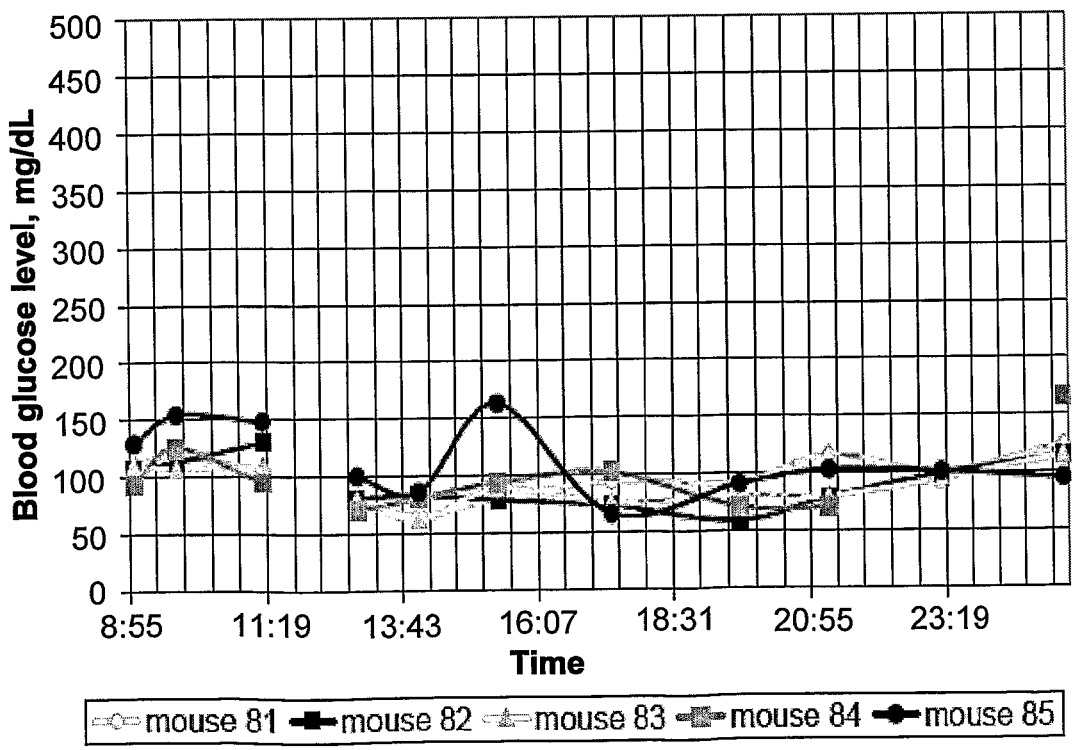

In a second experiment, an insulin composition (Formulation IV) of the present invention was administered orally to STZ-treated mice by gavage (1 ml volume) in dosages ranging from 2-10 IU. A dose-responsive reduction in blood glucose levels was observed for 9-12 hours; however, levels rarely dropped below 100 mg/dL (FIG. 8A-D). The presence of human insulin in the blood following administration of the insulin matrix carrier composition was confirmed by ELISA. By contrast, subcutaneous injection of 10 IU of insulin caused near-fatal hypoglycemia (FIG. 8E). Normal mice receiving 2, 5, or 10 IU insulin matrix carrier compositions exhibited only a slight reduction in blood glucose level (FIG. 8F), while those receiving injected insulin experienced a precipitous and occasionally fatal drop in glucose levels. As before, STZ-treated mice that received empty matrix carrier compositions (lacking insulin), orally administered insulin, or were left untreated did not exhibit significant blood glucose level reduction.

Figure 8G:
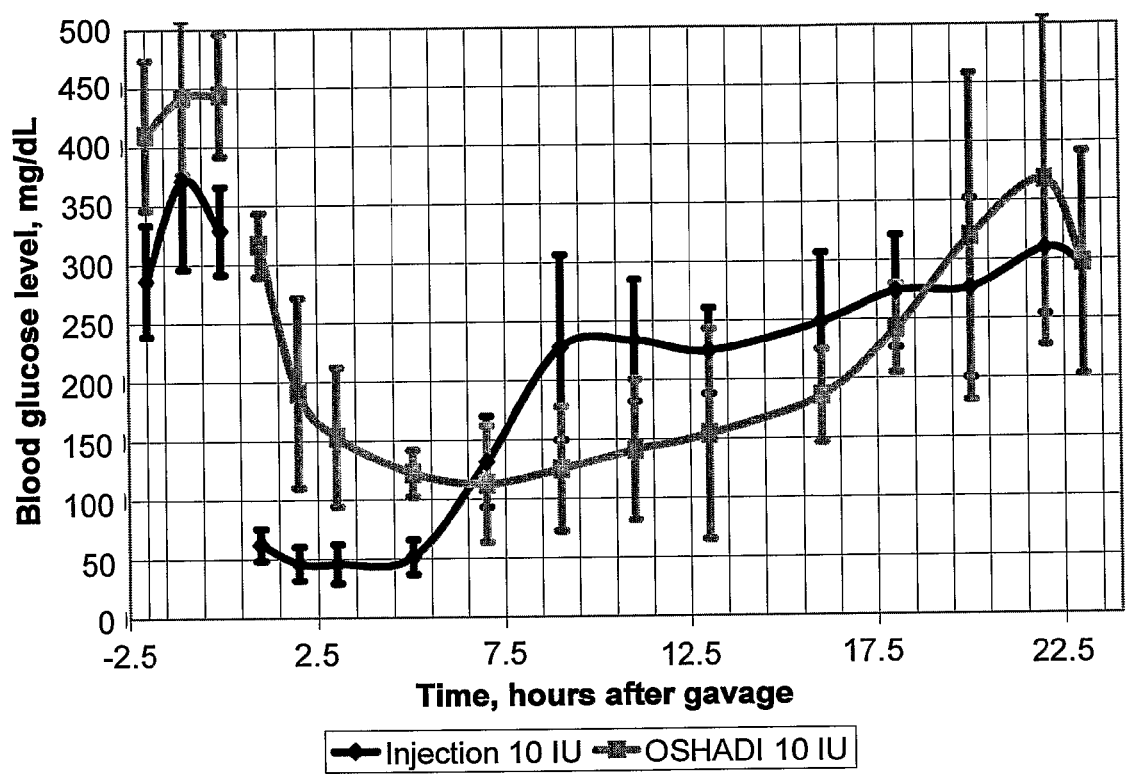
Figure 8H:
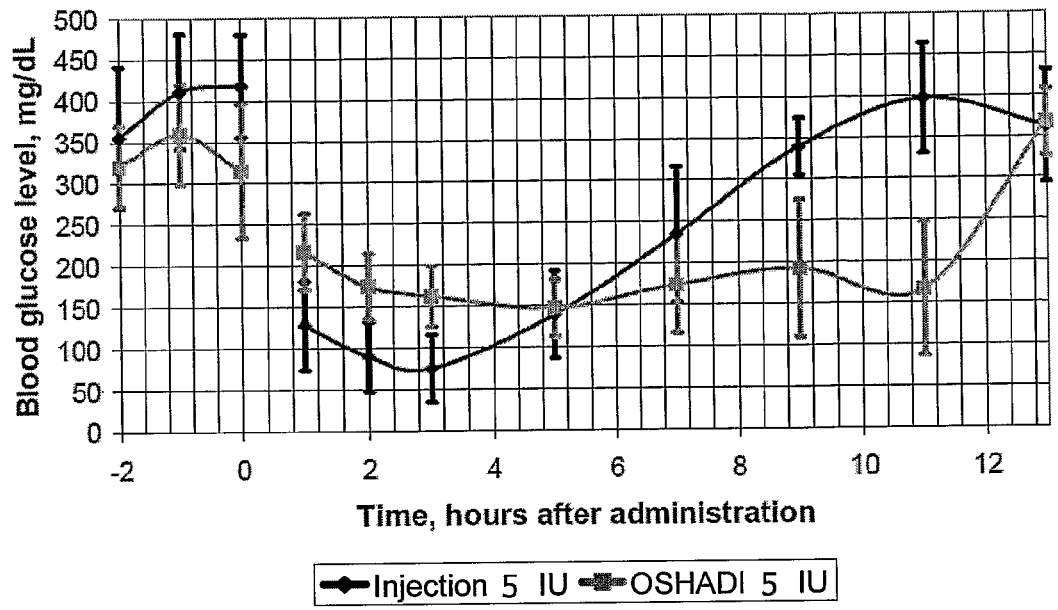
Figure 8I:
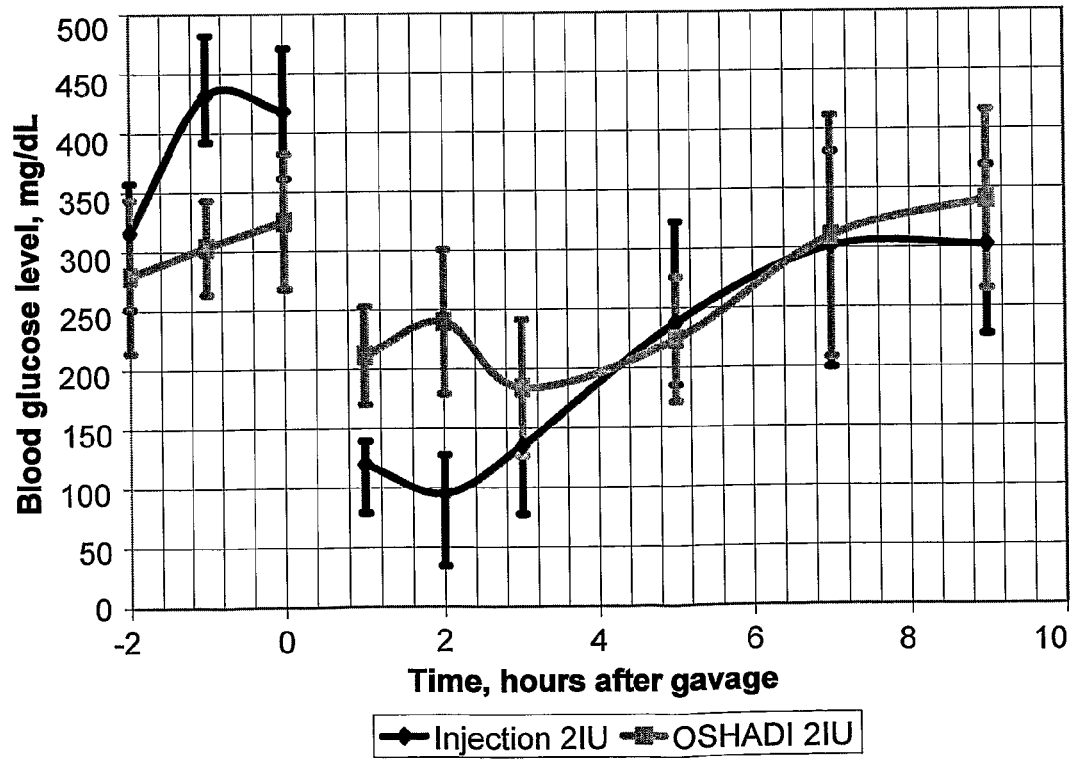

In another experiment, direct comparison of 10, 5, or 2 IU of insulin matrix carrier composition (Formulation IV) vs. injection of the same amount of insulin solution (the standard formulation) in 14-25 g mice reveled that mice treated with the oral insulin composition of the present invention maintained normal blood glucose levels for longer periods of time compared to the insulin injected mice. These observations reflect on the increased bioavailability of insulin when administered within the matrix carrier composition of the present invention. In addition, mice administered the matrix carrier compositions had no hypoglycemia, while the injected mice exhibited severe hypoglycemia (FIGS. 8G, H, I for 10, 5, and 2 IU, respectively).

Indication for the increased bioavailability of the insulin administered orally using the compositions of the present invention in comparison with injected insulin can be found by calculating the "Effective Areas". "Effective Area" is defined as the sum of the net changes in blood glucose level (BGL) values relative to the basal level, along a defined period of time, calculated as follows:
1. Obtain a baseline average of BGL for each time point.
2. For each time point, subtract the BGL value in the treated groups (oral insulin composition of the present invention and injected insulin) from the baseline average.
3. Sum the values obtained in step 2 for all time points.

To obtain the values in the table 3, the "effective areas" calculated of different treatments were then subtracted or divided.

TABLE 3

Effective Areas of insulin oral matrix carrier compositions versus injected insulin.

| Group | Value |
| --- | --- |
| 10 IU: (injection- matrix carrier composition) | −1042.7 mg/dL |
| 5 IU: (injection- matrix carrier composition) | 340.29 mg/dL |
| 2 IU: (injection- matrix carrier composition) | 834.4 mg/dL |
| 10 IU: injection/matrix carrier composition | 0.64 |
| 5 IU: injection/matrix carrier composition | 1.32 |
| 2 IU: injection/matrix carrier composition | 3.73 |
| 10 IU injection/5 IU injection | 1.32 |
| 10 IU injection/2 IU injection | 1.61 |
| 10 IU matrix carrier composition/5 IU matrix carrier composition | 2.74 |
| 10 IU matrix carrier composition/2 IU matrix carrier composition | 9.45 |

As shown in Table 3, the relatively low 10 IU/5 IU and 10 IU/2 IU ratios for injected insulin indicate that these doses are approaching the saturation dose for the mice. By contrast, the relatively large ratios for the insulin matrix carrier composition indicate that it is far from the saturation doses. Thus, matrix carrier compositions of the present invention are more amenable to accurate dosing within their therapeutic range, compared with standard injected insulin formulations.

Figure 9A:
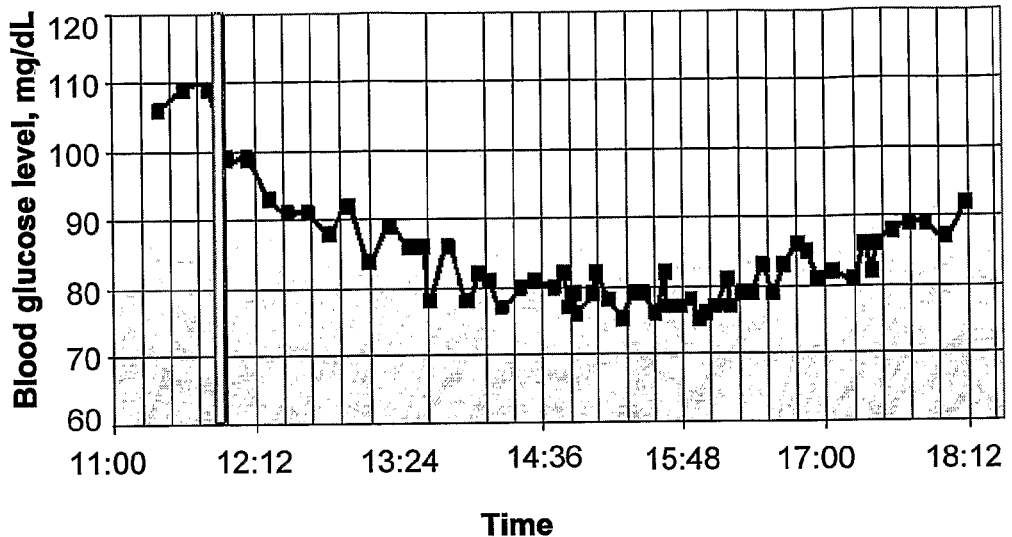
FIG. 9: Efficacy of insulin compositions on healthy (A) and diabetic (B) human subjects. A. 30 IU of the Actrapid relatively short-term release insulin matrix carrier formulation was administered at time 12:00, marked by the stripe in the graph. B. Daily average blood glucose levels. Gluco-Rite™ was administered on days 1-12. Insulin oral composition of the present invention was first administered on day 13 and continued for 14 days.

Next, the effect of the oral insulin composition of the present invention was tested on two human subjects, one healthy and one diabetic. 30 IU of Actrapid™ matrix carrier composition (Formulation II) reduced blood glucose levels in the healthy subject from 105 to 80-90 mg/dL over a six-hour test period (FIG. 9A). The subject reported an unusual degree of hunger, but otherwise no adverse reactions. By contrast, administration of injected insulin to healthy subjects is known to cause hypoglycemia, in some cases severe, with accompanying adverse reactions.

Figure 9B:
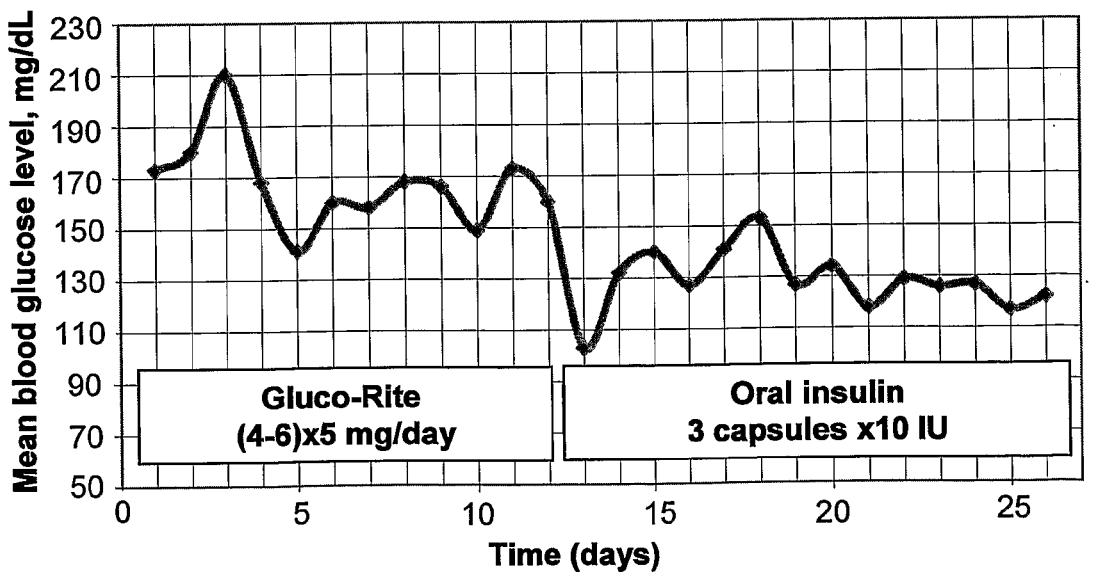

10 IU of the formulation V were administered 3 times per day over 14 days to a 67-year-old subject having type I/II diabetes, who exhibited glucose levels of over 170 when untreated and 130-170 when receiving Gluco-Rite™. Upon taking formulation V the blood glucose levels dropped to an average of about 130 (FIG. 9B). The subject reported feeling well during the entire period of receiving the oral insulin composition of the present invention. The subject has continued to take the compositions 3-4 times per day, as needed, resulting in well-controlled glucose levels with no adverse reactions. By contrast, the subject had a long-standing history of intense sensations of dread and unease after receiving a number of different injected insulin formulations.

The presence of elevated insulin levels in the diabetic subject's blood following administration of the insulin composition was confirmed by ELISA. Thus, matrix carrier compositions of the present invention are capable of orally delivering various forms of insulin in a biologically active form that can effectively treat diabetes. They have the additional advantage of not inducing hypoglycemia in either diabetic or normal subjects.

Example 8

Toxicity Study of Chronic Oral Administration of Insulin Compositions

Materials and Experimental Methods

Fifteen 10 week-old Balb/C male mice were used. Mice were administered daily 1 ml of insulin matrix carrier composition (25 IU/ml) (experimental group) or PBS (gavage control group) via gavage over 15 days. On the 14th and 15th day, mice were administered orally 100 ng of lipopolysaccharides (LPS) together with the insulin matrix carrier composition or PBS. Negative control mice were administered 1 ml PBS by gavage over 13 days, and 100 ng of LPS in 1 ml PBS by gavage on the 14th and 15th day. Positive control mice were injected with 1 mg of LPS in 1 ml of PBS. 3 h after LPS administration, mice were sacrificed, blood was collected (for LPS detection) and gastro-system, liver and kidneys were fixed in paraformaldehyde (PFA) 4% for histological analysis.

Animal follow up and macroscopic analysis: Mice were weighed every 3 days, and their fur condition was detected daily. After sacrifice, all organs or tissues were investigated for the presence of pathological changes Internal organs collection and fixation: On day 15 mice were sacrificed, and their gastro-system, kidney, and liver were collected from the abdominal cavity, weighed and fixed in 10% formalin solution.

Blood collection and plasma preparation: Blood was collected from the heart of the mice into tubes that contain EDTA. Plasma was be separated from the blood by centrifugation; at first for 15 min at 3000×gmax followed by 15 min at 16,000×gmax. Supernatant was removed, placed in a new tube and stored at −20° C.

Detection of LPS in mouse serum: LPS in mouse serum was detected by HPLC. Sera taken on day 15 from the groups described above were prepared for HPLC analysis by addition of 0.1M of EDTA.

Results

The toxicity of chronic administration of oral insulin compositions of the present invention was investigated. No pathological changes were observed in the animals' behavior. Their fur was in normal condition, appearing smooth, clean, and bright. No weight loss was detected; the mice gained weight normally.

Figure 10A:
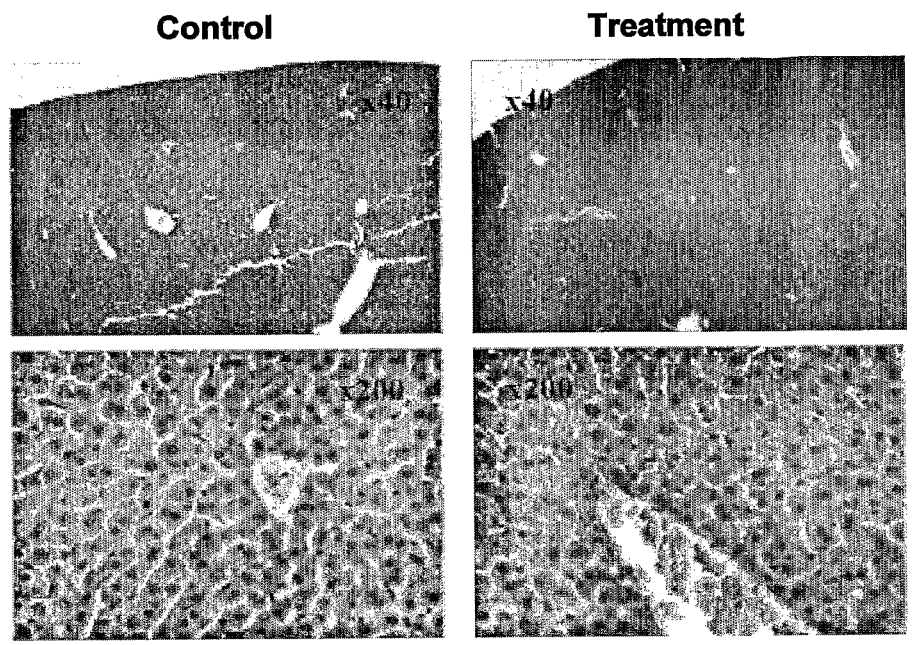
FIG. 10: Toxicity study of insulin compositions. Microscopic analysis of liver (A); kidney (B); and duodenum (C). In each case, left panels are control samples and right panels are treated samples. For A-B, top and bottom panels are 40× and 200× magnification, respectively. For C, top and bottom panels are 100× and 200× magnification, respectively.
Figure 10B:
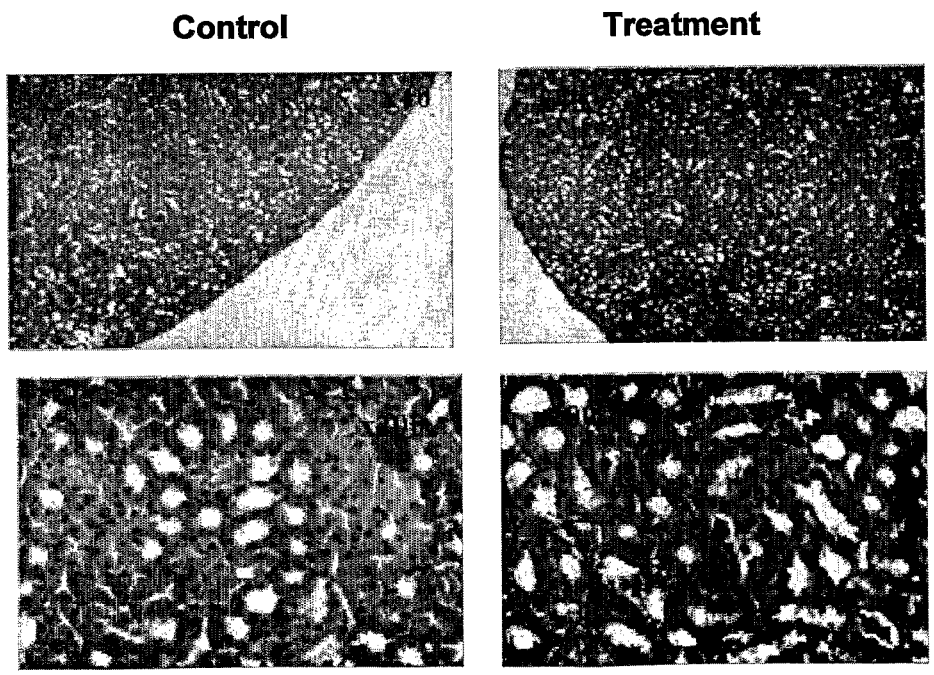
Figure 10C:
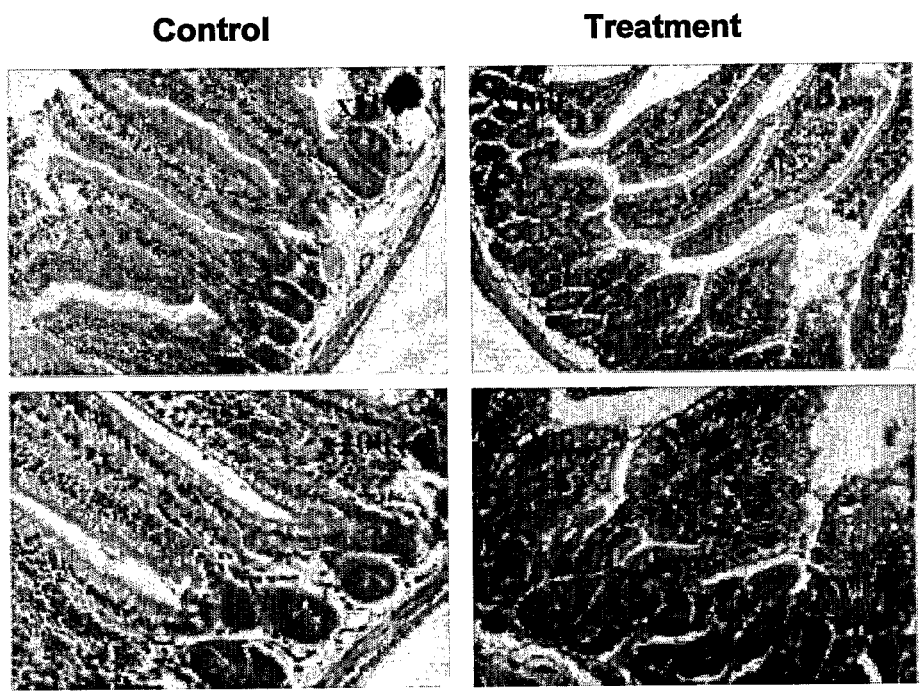

Macroscopic Analysis:

Macroscopic analysis of internal organs revealed no evidence of any pathology. Organs of all mice were normally developed, had normal size, shape, appearance (bright and smooth), and weight, were normally colored, and were in their normal location. Microscopic analysis showed no evidence of pathology in tissues of mice in all groups (liver—FIG. 10A; kidney—FIG. 10B; duodenum—FIG. 10C).

Figure 11A:
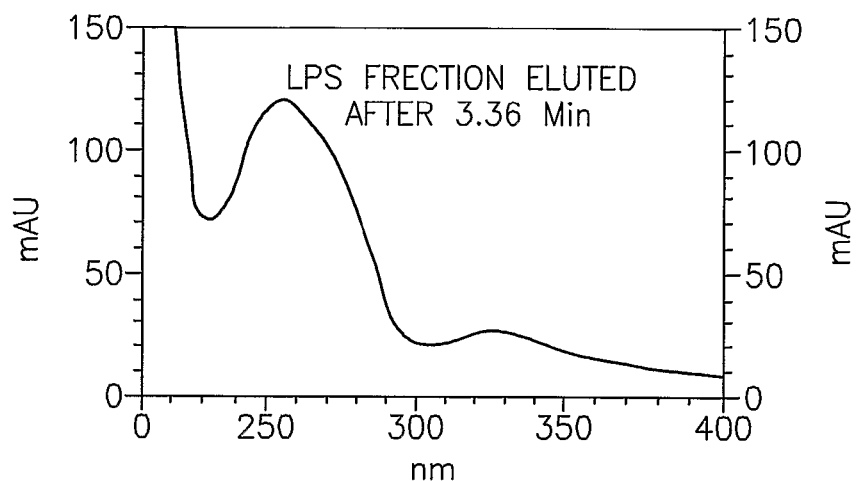
FIG. 11: A. Setup for HPLC analysis of lipopolysaccharide (LPS): B. Results of analysis: Positive control serum: mouse injected with 1 mg LPS (curve A); Negative control serum: mouse given no treatment (curve B); serum of mouse given orally (by gavage) insulin oral composition of the present invention on days 1-15 together with 1 mg LPS on days 14 & 15 (curve C); and mouse given orally on days 1-15 1 ml PBS, containing 1 mg LPS on days 14 & 15 (curve D).
Figure 11B:
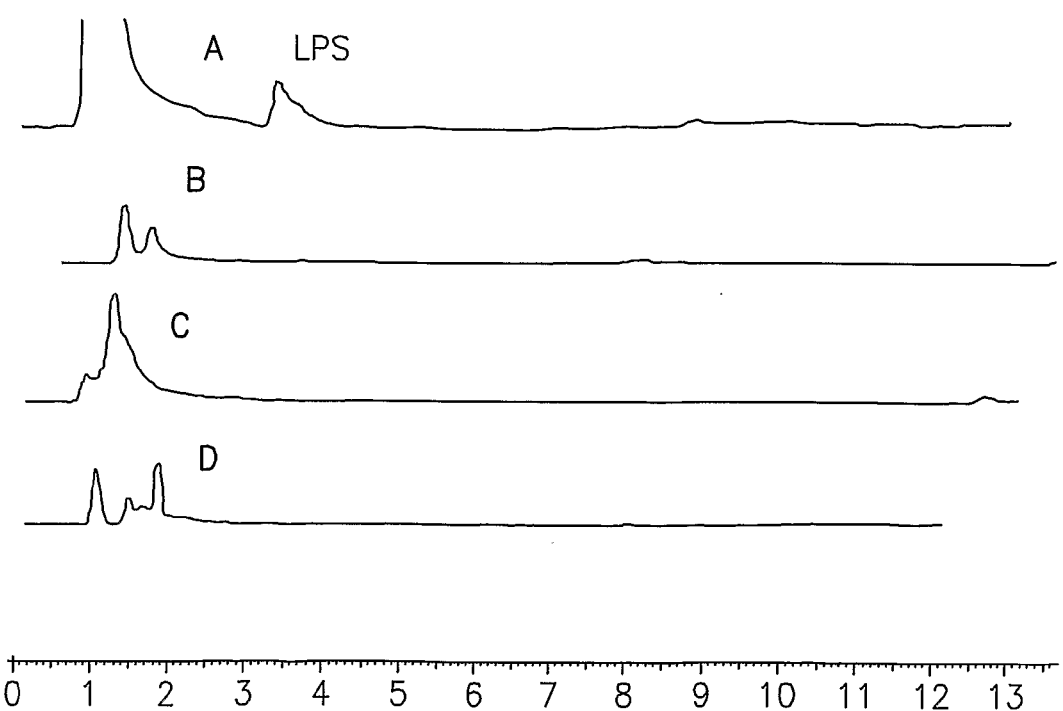

Serum from the treated and untreated mice were also tested for the presence of LPS. LPS was not present in serum of mice given oral insulin composition of the present invention+LPS (FIG. 11, curve C), nor in serum of mice given 1 ml PBS+LPS (FIG. 11, curve D), showing that neither the matrix carrier composition nor the gavage compromised the integrity of the mice's gastrointestinal linings. Serum from mice injected 1 mg of LPS in 1 ml of PBS served as a positive control (FIG. 11, curve A), and untreated mice served as negative control (FIG. 11, curve B).

Example 9

Preparation of Erythropoietin Matrix Carrier Composition

An erythropoietin (EPO) matrix carrier composition was produced, using the following ingredients:
EPREX™ epoetin alpha, 1 ml
Olive oil, 7 ml
Ambrotose™, 0.6 g
Silica, 0.1 g
Oblepicha oil, 8 ml
Linseed oil
The composition was prepared as described above in previous Examples. The volume in this composition was brought up to 20 ml with linseed oil. The final EPO concentration was 150 IU/ml.

Example 10

In Vivo Release Profile of Erythropoietin Matrix Carrier Composition

Figure 12:
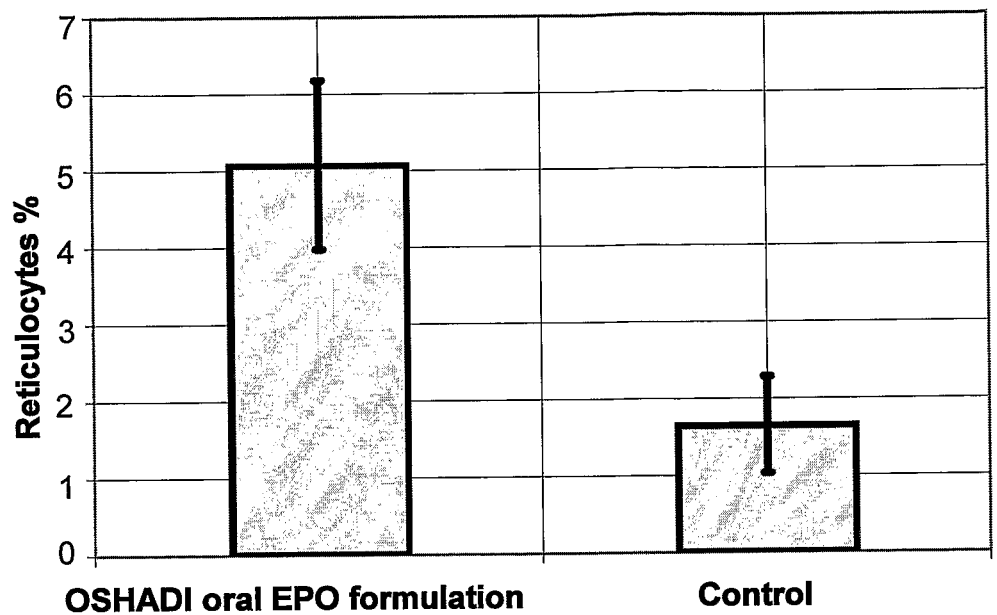
FIG. 12: Reticulocyte formation level in rats following administration of an erythropoietin (EPO) matrix carrier composition of the present invention. Vertical axis-relative reticulocyte count (% of reticulocytes (immature red cells) from mature red blood cells).

The in vivo release profile of the EPO matrix carrier composition from Example 9 was determined in rats. Relative reticulocyte count was measured after oral administration of matrix composition containing 200 IU EPO. The EPO composition was administered twice on days 1 and 4 of the study; blood samples were drawn on day 10 (2 doses; 5 rats). As a control, matrix carrier without EPO was administered (5 rats). Administration of the EPO matrix carrier potently stimulated reticulocyte formation (FIG. 12).

Example 11

Figure 13:
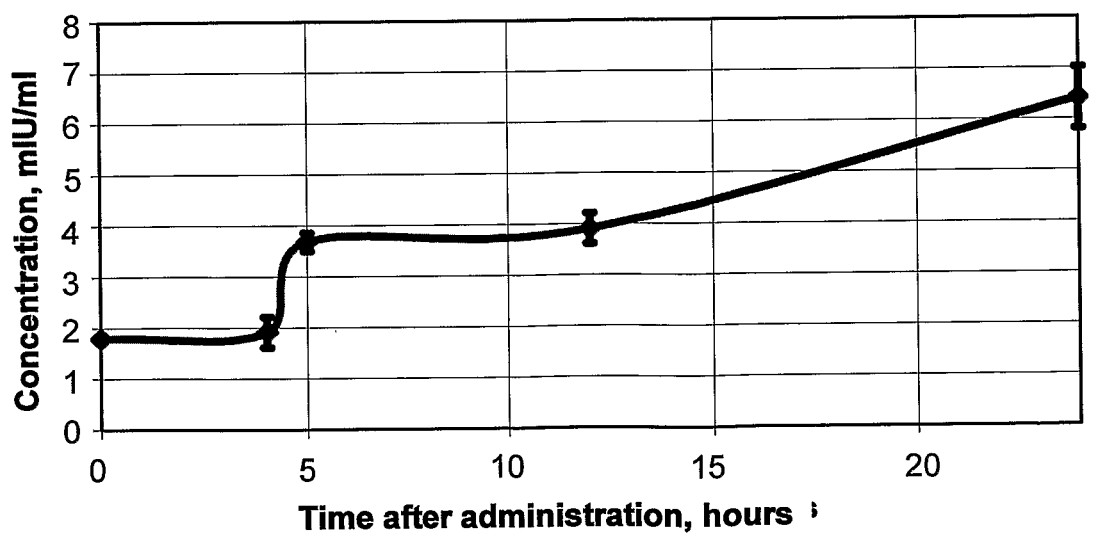
FIG. 13: EPO concentration in rat serum after oral administration of 150 IU EPO oral composition of the present invention.

EPO Activity in Normal and Anemic Rats Administered Erythropoietin Matrix carrier Composition Male SD rats were subjected to nephrectomy surgery removing 5/6 of the kidneys, to serve as a kidney failure model; control rats were left intact. 1 ml of the EPO matrix carrier composition from Example 9 was administered orally to rats by gavage, overall 150 IU EPO were administered. EPO levels were measured by ELISA (Human EPO Immunoassay by Quantikine™ IVD) at various time points between 1-24 hours after EPO administration. The EPO was efficiently absorbed by both normal and nephrectomy rats (FIG. 13).

In other experiments, 150 IU EPO was either administered orally in a matrix carrier composition on days 1 and 5 or was administered subcutaneously on days 1 and 5. Reticulocyte and hemoglobin blood counts were performed at different times between 2-5 weeks after EPO administration. The EPO matrix carrier composition was equally effective as the injected EPO. Data from a representative time point is depicted in Table 4.

TABLE 4

Comparison of the average long term effect (one month from the first EPO administration) of oral administration of EPO matrix carrier composition vs. SC injection of EPO.

|      | oral EPO | SC injected EPO |
| ---- | -------- | --------------- |
| WBC  | 4.02     | 1.86            |
| RBC  | 7.968    | 7.436           |
| HGB  | 14.84    | 14.18           |
| HCT  | 43.08    | 40.66           |
| MCV  | 54.08    | 54.66           |
| MCH  | 18.62    | 18.968          |
| MCHC | 34.46    | 34.84           |
| RDW  | 13.16    | 18.62           |
| PLT  | 760.4    | 708.2           |
| MPV  | 4.96     | 4.84            |
| RET %| 3.674    | 3.034           |
| RET# | 0.2941   | 0.22578         |

Example 12

Preparation of a Growth Hormone (GH) Matrix Carrier Composition

A Growth Hormone (GH) matrix carrier composition was produced, using the following ingredients:

| Growth hormone powder- see below | 24 mg |
| Amylopectin from maize (Fluka catalog number 22720) | 3.5 gr |
| Silica R972 | 0.7 gr |
| Olive oil | 20 ml |
| Oblepicha oil | 30 ml |
| Sesame oil | up to 70 ml |

Genotropin™ growth hormone was obtained from Pharmacia and Upjohn, in the form of a lyophilized Powder containing somatropin [rDNA origin], which is a polypeptide hormone of recombinant DNA origin. It has 191 amino acid residues and a molecular weight of 22,124 daltons. The amino acid sequence of the product is identical to that of human growth hormone of pituitary origin (somatropin).

Example 13

Medium-term Release TGF-β Matrix Carrier Composition

The following formulation was designed for medium-term TGF-β release: 30 ml of sesame oil and 120 ml of sea buckthorn (oblepicha) oil were combined in a beaker and stirred for 3 minutes (min) at 60 rpm with a magnetic stirrer. 20 grams (g) TGF-β (53 kD) was stirred into the oil mixture at 20 rpm for 4 min, then 60 rpm for 7 min. 18 g amylopectin from maize (Fluka catalog number 22720) was weighed with an analytical scale, combined with 3 g hydrophobic silica fumed R972 (Degussa Inc), and mixed by vortexing at 900 rpm for 5 min. Association between the amylopectin and the silica was determined by the mixture's ability to float after being placed on the surface of a water-filled beaker. The amylopectin/silica mixture was added to the oil-TGF-β solution and stirred for 25 minutes at 40 rpm. 75 ml olive oil were added, and the mixture was stirred at 50 rpm for 3 min. The volume was brought up to 300 ml with sesame oil, and the mixture was stirred at 50 rpm for 20 min. The product was stored refrigerated (3-8° C.).

In some experiments, the product is packaged into gelatin enteric covering capsules, such as those commercially available from Shionogi and Company, Ltd, Japan.

Example 14

Preparation of a Copaxone™ Matrix Carrier Composition

A Copaxone™ composition (Copaxone-Formulation I) is produced, using the following ingredients:
Copaxone powder, 5 g
Jojoba oil 40 ml
Olive oil, 50 ml
Alpha-glucan, 2 g
Beta-glucan, 2 g
Amylopectin 7 g
Silica R972, 2 g
Sea buckthorn oil, 80 ml
Sesame Oil up to 200 ml
 1. Mix alpha and beta-glucan with amylopectin for 10 minutes.
 2. Add silica R972 and mix intensively for 15 minutes.
 3. Check the quality of the mixture by wetting (powder must float on the water surface without moistening).
 4. Mix Sea buckthorn (Oblepicha) Oil and Jojoba Oil for 5 minutes.
 5. Add the Copaxone powder to the Sea buckthorn and jojoba oil mixture. Mix gently using circular movement for 15 minutes.
 6. Add the mixture from step 2 to the Copaxone mixture from step 5 and mix gently by circular movement for 25 minutes.
 7. Add Olive Oil and Sesame Oil, and mix using a magnetic stirrer for 40 minutes.

Next, an additional Copaxone™ composition (Copaxone-Formulation II) is produced, using the following ingredients:
Copaxone™ powder, 5 g
Sea Buckthorn oil 30 ml
Olive oil, 50 ml
Beta-glucan, 4 g
Amylopectin 7 g
Silica R972, 2 g
Beeswax, 170 g
Procedure:
1. Mix beta-glucan with amylopectin for 10 minutes.
2. Add silica R972 and mix intensively for 15 minutes.
3. Check the quality of the mixture by wetting (powder must float on the water surface without moistening).
4. Mix Sea buckthorn (Oblepicha) Oil and Olive Oil for 5 minutes.
5. Add Copaxone™ powder to Sea buckthorn and Olive oil mixture. Mix gently by circular movement for 15 minutes
6. Add the mixture of step 2 to the Copaxone mixture of step 5 and mix gently by circular movement for 25 minutes.
7. Heat beeswax, pulverized it and combine with the oil suspension of step 6. Mix and cool.

Example 15

Preparation of an Apolipoprotein A-1-Mimetic Peptide Matrix Carrier Composition An apolipoprotein A-1-mimetic peptide composition is produced, using the following ingredients:
APO A-1-mimetic peptide powder, 11 g
Sea Buckthorn oil 50 ml
Olive oil, 50 ml
Beta-glucan, 3 g
Chitin, 2 g
Amylopectin 8 g
Silica R972, 4.5 g
Beeswax, 140 g
Procedure:
1. Mix beta-glucan with chitin and amylopectin for 10 minutes.
2. Add silica R972 and mix intensively for 15 minutes.
3. Check the quality of the mixture by wetting (powder must float on the water surface without moistening).
4. Mix Sea buckthorn (Oblepicha) Oil and Olive Oil for 5 minutes.
5. Add Apolipoprotein A-1 powder to the Sea buckthorn and Olive oil mixture. Mix gently, using a circular movement 25 minutes.
6. Add the mixture of step 2 to the Apolipoprotein A-1 mixture of step 5. Mix gently using circular movement for 30 minutes.
7. Heat beeswax, pulverized it and combine with the oil suspension of step 6. Mix and cool.

Example 16

Preparation of a Rituxan® (Therapeutic Monoclonal Antibody) Matrix Carrier Composition A Rituxan® (MabThera) is produced, using the following ingredients:
Lyophilized Rituxan powder, 7 g
Sea Buckthorn oil 40 ml
Olive oil, 40 ml
Chitin, 3 g
Amylopectin 8 g
Silica R972, 3.2 g
Beeswax, 140 g
Procedure:
1. Mix chitin and amylopectin for 10 minutes.
2. Add silica R972 and mix intensively for 15 minutes.
3. Check the quality of the mixture by wetting (powder must float on a water surface without moistening).
4. Mix Sea buckthorn (Oblepicha) Oil and Olive Oil for 5 minutes.
5. Add the Rituxan® powder to the Sea buckthorn and Olive oil mixture. Mix gently by circular movement for 15 minutes
6. Add the mixture of step 2 to the Rituxan mixture of step 5 and mix gently using a circular movement for 25 minutes.
7. Heat beeswax, pulverize it and combine with the oil suspension of step 6. Mix and cool.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An oral pharmaceutical composition, comprising an oil having particulate matter suspended therein, wherein the composition is not an emulsion and the particulate matter comprises:
   a. a polysaccharide comprising at least one branched polysaccharide selected from the group consisting of amylopectin, starch, glycogen and combinations thereof, wherein the polysaccharide is in non-covalent association with silica nanoparticles having a hydrophobic surface, wherein the size of the silica nanoparticles is between 1-100 nanometers and wherein the weight of the branched polysaccharide is at least twice that of the silica nanoparticles; and
   b. a protein or peptide having therapeutic activity, non-covalently associated with said silica nanoparticles and the polysaccharide.

2. The pharmaceutical composition of claim 1, wherein said composition is anhydrous.

3. The pharmaceutical composition of claim 1, wherein said size of said silica nanoparticles is between 5-30 nanometers.

4. The pharmaceutical composition of claim 1, wherein said hydrophobic surface of said silica nanoparticles comprises hydrocarbon moieties.

5. The pharmaceutical composition of claim 1, further comprising a structural protein selected from the group consisting of elastin, collagen, keratin, fibrinogen and combinations thereof.

6. The pharmaceutical composition of claim 1, further comprising an amino acid selected from the group consisting of arginine, lysine, glutamic acid, aspartic acid, histidine and combinations thereof.

7. The pharmaceutical composition of claim 1, wherein said oil comprises a mixture of oils.

8. The pharmaceutical composition of claim 1, wherein said oil comprises a mixture of oils selected from natural vegetable oils and synthetic oils.

9. The pharmaceutical composition of claim 1, wherein said composition further comprises an antioxidant.

10. The pharmaceutical composition of claim 1, wherein said protein or peptide is selected from a group consisting of: erythropoietin, pituitary growth hormone, glatiramer acetate, apolipoprotein A-1-mimetic peptide, monoclonal antibody against the protein CD20, calcitonin, a tumor necrosis factor (TNF) protein, interferon-alpha, interferon-beta, interferon-gamma, DNase, RNase, and combinations thereof.

11. The pharmaceutical composition of claim 1, wherein the weight of said particulate matter is not more than 25% of the volume of said pharmaceutical composition.

* * * * *